United States Patent
Lakhtakia et al.

(10) Patent No.: US 11,646,121 B2
(45) Date of Patent: May 9, 2023

(54) SYSTEMS AND METHODS FOR ANALYZING AND VALIDATING PATIENT INFORMATION TRENDS

(71) Applicant: Flatiron Health, Inc., New York, NY (US)

(72) Inventors: Shreyas Lakhtakia, New York, NY (US); Daniel Obeng, Baltimore, MD (US); Sharon Moon, New York, NY (US); Andrew Dempsey, Astoria, NY (US); Breno Neri, Darien, CT (US); Joseph Brown, Madison, NJ (US); James Tyler Martineau, Santa Monica, CA (US)

(73) Assignee: Flatiron Health, Inc., New York, NY (US)

( * ) Notice: Subject to any disclaimer, the term of this patent is extended or adjusted under 35 U.S.C. 154(b) by 0 days.

(21) Appl. No.: 17/307,748

(22) Filed: May 4, 2021

(65) Prior Publication Data

US 2022/0359087 A1    Nov. 10, 2022

(51) Int. Cl.
  *G16H 50/70*    (2018.01)
  *G06N 3/08*    (2006.01)
  *G06F 16/23*    (2019.01)
  *G16H 10/60*    (2018.01)

(52) U.S. Cl.
  CPC ......... *G16H 50/70* (2018.01); *G06F 16/2365* (2019.01); *G06N 3/08* (2013.01); *G16H 10/60* (2018.01)

(58) Field of Classification Search
  CPC .... G16H 50/70; G16H 10/60; G06F 16/2365; G06N 3/08
  See application file for complete search history.

(56) References Cited

U.S. PATENT DOCUMENTS

| | | | |
|---|---|---|---|
| 7,536,044 B2 * | 5/2009 | Zhou ................... | G06V 10/754 382/128 |
| 7,650,321 B2 * | 1/2010 | Krishnan ............... | G16H 50/20 706/20 |

(Continued)

OTHER PUBLICATIONS

Zhang et al., MedMon: Securing Medical Devices Through Wireless Monitoring and Anomaly Detection, IEEE Transactions on Biomedical Circuits and Systems, vol. 7, No. 6, Dec. 2013, pp. 871-881.*

*Primary Examiner* — Jay M. Patel
(74) *Attorney, Agent, or Firm* — Finnegan, Henderson, Farabow, Garrett & Dunner, LLP.

(57) ABSTRACT

A system for classifying patient parameter values may include at least one processor programmed to access first information associated with a plurality of patients, the first information including a plurality of patient parameters associated with the plurality of patients, the first information being accessed electronically via a database; determine a first value associated with a patient parameter of at least one of the plurality of patients; analyze second information associated with at least one patient to determine a second value of the patient parameter; detect, based on analysis of at least the first value and the second value, a potential anomaly in the second value; and cause a graphical user interface of a computing device to display at least one graphical element indicating the potential anomaly.

15 Claims, 11 Drawing Sheets

(56) References Cited

U.S. PATENT DOCUMENTS

| | | | | |
|---|---|---|---|---|
| 7,653,227 | B2* | 1/2010 | Krishnan | G16H 50/20 382/128 |
| 7,949,167 | B2* | 5/2011 | Krishnan | G16H 50/70 382/128 |
| 7,965,869 | B2* | 6/2011 | Zhou | G06T 7/251 382/128 |
| 8,494,238 | B2* | 7/2013 | Zhou | G06K 9/00 382/128 |
| 11,271,957 | B2 | 3/2022 | Kulkarni et al. | |
| 2005/0049497 | A1* | 3/2005 | Krishnan | G16H 50/20 600/437 |
| 2005/0147303 | A1* | 7/2005 | Zhou | G06V 10/754 382/128 |
| 2005/0209519 | A1* | 9/2005 | Krishnan | G16H 50/20 600/437 |
| 2006/184475 | A1* | 8/2006 | Krishnan | G16H 50/20 706/20 |
| 2007/0118399 | A1* | 5/2007 | Avinash | G16H 40/20 705/2 |
| 2009/0310836 | A1* | 12/2009 | Krishnan | G06T 7/0012 382/128 |
| 2011/0188706 | A1* | 8/2011 | Zhou | G06K 9/00 382/103 |
| 2012/0051608 | A1* | 3/2012 | Avinash | G06T 7/11 382/128 |
| 2014/0324469 | A1* | 10/2014 | Reiner | G16H 50/70 705/3 |
| 2016/0267222 | A1* | 9/2016 | Larcom | G16H 30/20 |
| 2021/0037031 | A1* | 2/2021 | Kulkarni | G06F 17/18 |

* cited by examiner

Figure 4A:
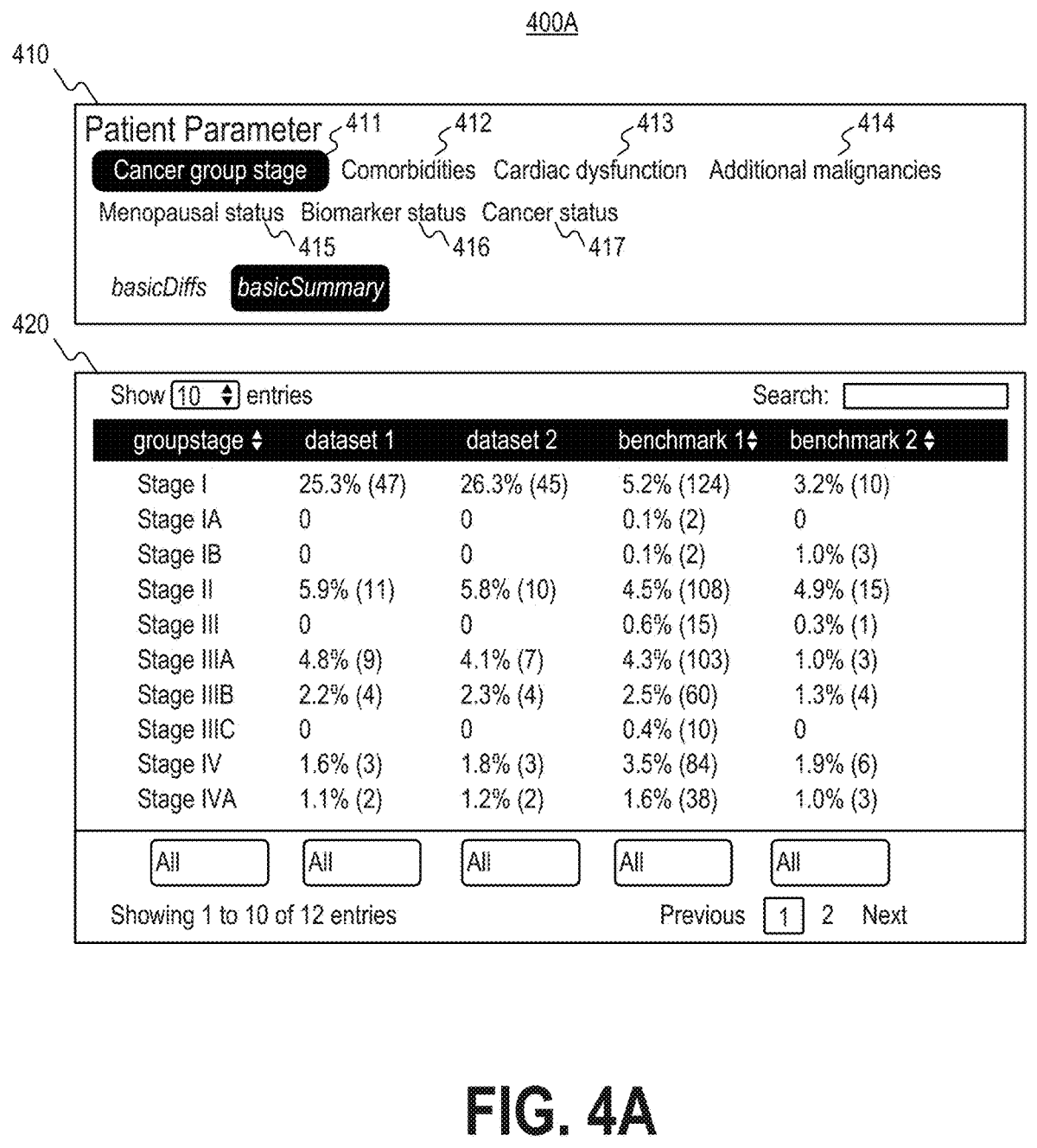

400A

410

Patient Parameter 411 412 413 414
[Cancer group stage]   Comorbidities   Cardiac dysfunction   Additional malignancies
Menopausal status   Biomarker status   Cancer status
415   416   417

*basicDiffs*   [*basicSummary*]

420

Show [10 ▾] entries                                              Search: [      ]

| groupstage ⇕ | dataset 1 | dataset 2 | benchmark 1 ⇕ | benchmark 2 ⇕ |
|---|---|---|---|---|
| Stage I | 25.3% (47) | 26.3% (45) | 5.2% (124) | 3.2% (10) |
| Stage IA | 0 | 0 | 0.1% (2) | 0 |
| Stage IB | 0 | 0 | 0.1% (2) | 1.0% (3) |
| Stage II | 5.9% (11) | 5.8% (10) | 4.5% (108) | 4.9% (15) |
| Stage III | 0 | 0 | 0.6% (15) | 0.3% (1) |
| Stage IIIA | 4.8% (9) | 4.1% (7) | 4.3% (103) | 1.0% (3) |
| Stage IIIB | 2.2% (4) | 2.3% (4) | 2.5% (60) | 1.3% (4) |
| Stage IIIC | 0 | 0 | 0.4% (10) | 0 |
| Stage IV | 1.6% (3) | 1.8% (3) | 3.5% (84) | 1.9% (6) |
| Stage IVA | 1.1% (2) | 1.2% (2) | 1.6% (38) | 1.0% (3) |

[All]   [All]   [All]   [All]   [All]

Showing 1 to 10 of 12 entries                    Previous [1] 2 Next

Patient Parameter

Cancer group stage | Comorbidities | Cardiac dysfunction | Additional malignancies
Menopausal status | Biomarker status | Cancer status

*basicDiffs* | *basicSummary* | vs – Jul2018 – Diffs | vs – Jul2018 – Summary
vs – Jul2018 – Within – patientChanges Show 10 entries     Search: _____

| biomarker X | Feb2018 | Jul2018 |
|---|---|---|
| No | 48.3% (41) | 0% (4287) |
| Untested | 29.8% (2584) | 27.9% (2395) |
| Yes | 22.0% (1906) | 22.2% (1912) |

| All | All | All |

Showing 1 to 3 of 3 entries     Previous [1] Next

FIG. 4B

QA Report

Date generated: 21 June, 2019
Diseases in review: 4 total – disease_1, disease_2, disease_3, disease_4

General Alerts 0 section(s) of the data were found to have no patient-data for the cohorts of interest – please investigate manually if needed:

Show [15 ▼] entries                                                                 Search: [          ]

| disease ◆ | cohort_current ◆ | cohort_comparison ◆ | section ◆ |
|---|---|---|---|
| | | No data available in table | |

Showing 0 to 0 of 0 entries                                                       Previous   Next

Overall Cohort Changes

Show [15 ▼] entries                                                                 Search: [          ]

| | disease ◆ | section ◆ | variable ◆ | value ◆ | absolute_diff ◆ | % Dataset1 ◆ | % Dataset2 ◆ | # Dataset1 ◆ | # Dataset2 ◆ |
|---|---|---|---|---|---|---|---|---|---|
| | [2 ⊗] | [All] | [pdl1] | [All] | [All] | [All] | [All] | [All] | [All] |
| 1 | disease_2 | BiomarkerStatus | pdl1_tested | Missing | 100.00% | 100.00% | 0.00% | 180 | 0 |
| 4 | disease_2 | BiomarkerStatus | pdl1_tested | False | -97.74% | 0.00% | 97.74% | 0 | 130 |
| 80 | disease_2 | BiomarkerStatus | pdl1_tested | Yes | 4.41% | 6.67% | 2.26% | 12 | 3 |
| 81 | disease_2 | BiomarkerStatus | pdl1_status | Not tested | -4.41% | 93.33% | 97.74% | 168 | 130 |
| 82 | disease_2 | BiomarkerStatus | pdl1_tested | No | -4.41% | 93.33% | 97.74% | 168 | 130 |
| 153 | disease_2 | BiomarkerStatus | pdl1_status | PD-L1 negative | 2.58% | 3.33% | 0.75% | 6 | 1 |
| 184 | disease_2 | BiomarkerStatus | pdl1_tested | True | -4.26% | 0.00% | 2.26% | 0 | 3 |
| 256 | disease_2 | BiomarkerStatus | pdl1_status | PD-L1 positive | 1.47% | 2.22% | 0.75% | 4 | 1 |
| 516 | disease_2 | BiomarkerStatus | pdl1_status | No interpretation | 0.36% | 1.11% | 0.75% | 2 | 1 |

Showing 1 to 3 of 3 entries                                                       Previous [1] Next

Anomalies Detected

Show [15 ▼] entries      Search: [ ]

| | disease | | section | |
|---|---|---|---|---|
| | All | | All | |
| 1 | Disease_1 | Patient Parameter | Biomarker X | SD away from mean diff |
| 2 | Disease_1 | Patient Parameter | Comorbidity X | SD away from mean diff |
| 3 | Disease_1 | Patient Parameter | Cardiac dysfunction | Value absent |

Showing 1 to 3 of 3 entries      Previous [1] Next

FIG. 6A

SYSTEMS AND METHODS FOR ANALYZING AND VALIDATING PATIENT INFORMATION TRENDS

BACKGROUND

Technical Field

The present disclosure relates to systems and methods for classifying patient parameter values. In particular, the present disclosure provides a dataset validation tool for automatically surfacing potential anomalies to a user and facilitating review of the potential anomalies.

Background Information

Medical research, such as studies that may concentrate on disease diagnosis, disease treatment, drug efficacy, etc., often involves the analysis of large data sets collected relative to many patients. As data is collected, these data sets may continue to grow and/or evolve. For every iteration of the data set, however, it is important that the data sets remain accurate and useful for research studies. Data sets that include data anomalies relative to one or more parameters may negatively impact research studies, may degrade training processes for neural networks, and may cascade into incorrect medical conclusions. Thus, there is a need for validating each iteration of an assembled data set after its assembly and before it is provided to researchers. The validation process may include various tests and analyses relative to one or more data parameters represented in a data set and/or relative to data values included in a particular data set, especially as compared to data values included in one or more prior iterations of the data set. Through data validation processes, data anomalies may be identified such that the anomalous data values may be excluded from the data set, one or more affected parameters may be updated, or any other pertinent adjustment to the data set may be made in order to, for example, increase the quality and/or veracity of the overall data set and increase its usefulness to researchers and others in the medical community.

In the past, such data quality and validation efforts, including anomaly identification and removal, have typically been performed through a laborious, manual inspection process. Specifically, humans would undertake the time-consuming task of inspecting the data sets, identifying potential anomalies within the data sets, and deciding, on an individual basis, whether there was a reasonable explanation for an observed anomaly in the data set.

The human inspector could identify potential anomalies in a number of ways. In some cases, the data set under inspection may be compared with earlier versions of the data set. This may include generating and reviewing a report comparing all variations of data values between data sets. Such reports were often very long, including thousands of pages or more, and a human inspector would need to traverse the entire document looking for potential anomalies. Such a process is extremely time consuming and, in many cases, not possible due to the volume of data and associated parameters that may be associated with a particular data set. It is a quintessential "needle in a haystack" problem. In many cases, human inspectors would only review a small subset of the parameters or reports, which meant that anomaly detection was limited in scope and covered a random sample of datasets.

Further, identification of anomalies depended on a human's ability to recognize a change in data values as an anomaly and not being attributable to normal variations in data. For example, as patient data will change with the passage of time (e.g., new patients may be added, more data may be collected for patients already a part of a study, etc.), the more recent data set may support intrinsic or derived parameter values (e.g., percentages of patients exhibiting a certain characteristic or the prevalence of a particular biomarker among the corpus, among potentially thousands or millions of other parameters that may be viewed or studied relative to a data set) that are different from those supported by earlier versions of the data set. In such cases, human reviewers would be responsible for analyzing the potentially thousands or millions of parameter values that may be of interest, determining whether any of the parameter values exhibit differences from one data set to the next that indicate a data anomaly, and then analyzing observed parameter value differences to determine if the observed differences have valid explanations or whether the differences result from unwanted data anomalies with the potential to degrade the data set.

In one example, if a recent version of a data set indicates that 1.0% of patients in the data set tested positive for a particular gene mutation, whereas in a prior version of the data set only 0.5% of patients tested positive for that gene mutation, then a human analyst would have to identify the 0.5% increase in this parameter value as something warranting further investigation. The analyst would then need to investigate to determine whether the 0.5 percent increase for the parameter is a reasonable increase supported by valid changes in the data set or whether the 0.5% increase results from a data anomaly. Typical workflow processes leave the entirety of the identification, analysis, and conclusion portions of the process to human judgment. Such analysis by the human inspector was very difficult, if not impossible, especially as many data anomalies may present as what appears to be less significant data value changes as compared to other valid data value changes. Further, humans become conditioned to miss actual issues when most variables tested are not anomalous and thus this process is prone to errors. As a further drawback, processes reliant upon humans to identify potential data anomalies may suffer from variability, as different human reviewers may evaluate the data and parameter values using different criteria.

As a result, the human-based data set verification and validation process may be insufficient for providing a suitable level of quality control relative to large data sets, which can result in erroneous data being used for research or other purposes. In view of these, and other deficiencies in existing techniques, technical solutions are needed for efficiently and accurately detecting anomalies in patient parameters. Specifically, solutions should provide an automated system for reviewing large quantities of data. Such solutions should surface to a user only those parameters that are determined as exhibiting potential anomaly and should facilitate interaction with the surfaced results by the user. Moreover, these technical solutions should also allow for automatic adjustment and learning of tolerances or other values to improve anomaly detection based on feedback from a user.

SUMMARY

Embodiments consistent with the present disclosure include systems and methods for classifying patient parameter values. Embodiments of the present disclosure may overcome one or more aspects of existing techniques for determining potential anomalies within patient information. The use of computer-generated algorithms in accordance with embodiments of the present disclosure thus allows for faster and more efficient ways for providing patients, physicians, and researchers with accurate and reliable patient data to use for research and other applications.

In an embodiment, a system for classifying patient parameter values may include at least one processor programmed to: access first information associated with a plurality of patients, the first information including a plurality of patient parameters associated with the plurality of patients the first information being accessed electronically via a database; determine a first value associated with a patient parameter of at least one of the plurality of patients; analyze second information associated with at least one patient to determine a second value of the patient parameter; detect, based on analysis of at least the first value and the second value, a potential anomaly in the second value; and cause a graphical user interface of a computing device to display at least one graphical element indicating the potential anomaly.

In an embodiment, a method for classifying patient parameter values may include accessing first information associated with a plurality of patients, the first information including a plurality of patient parameters associated with the plurality of patients, the first information being accessed electronically via a database; determining a first value associated with a patient parameter of at least one of the plurality of patients; analyzing second information associated with at least one patient to determine a second value of the patient parameter; detecting, based on analysis of at least the first value and the second value, a potential anomaly in the second value; and causing a graphical user interface of a computing device to display at least one graphical element indicating the potential anomaly.

In an embodiment, a non-transitory computer-readable medium may include instructions that when executed by one or more processors, cause the one or more processors to: access first information associated with a plurality of patients, the first information including a plurality of patient parameters associated with the plurality of patients, the first information being accessed electronically via a database; determine a first value associated with a patient parameter of at least one of the plurality of patients; analyze second information associated with at least one patient to determine a second value of the patient parameter; detect, based on analysis of at least the first value and the second value, a potential anomaly in the second value; and cause a graphical user interface of a computing device to display at least one graphical element indicating the potential anomaly.

BRIEF DESCRIPTION OF THE DRAWINGS

The accompanying drawings, which are incorporated in and constitute part of this specification, and together with the description, illustrate and explain the principles of various exemplary embodiments. In the drawings:

FIGS. 4A and 4B are diagrams illustrating exemplary user interfaces for providing patient information, consistent with the present disclosure.

FIGS. 5A, 5B, and 5C are diagrams illustrating exemplary user interfaces for surfacing patient information trends, consistent with the present disclosure.

FIGS. 6A and 6B are diagrams illustrating exemplary user interfaces for providing anomaly information, consistent with the present disclosure.

DETAILED DESCRIPTION

Figure 1:
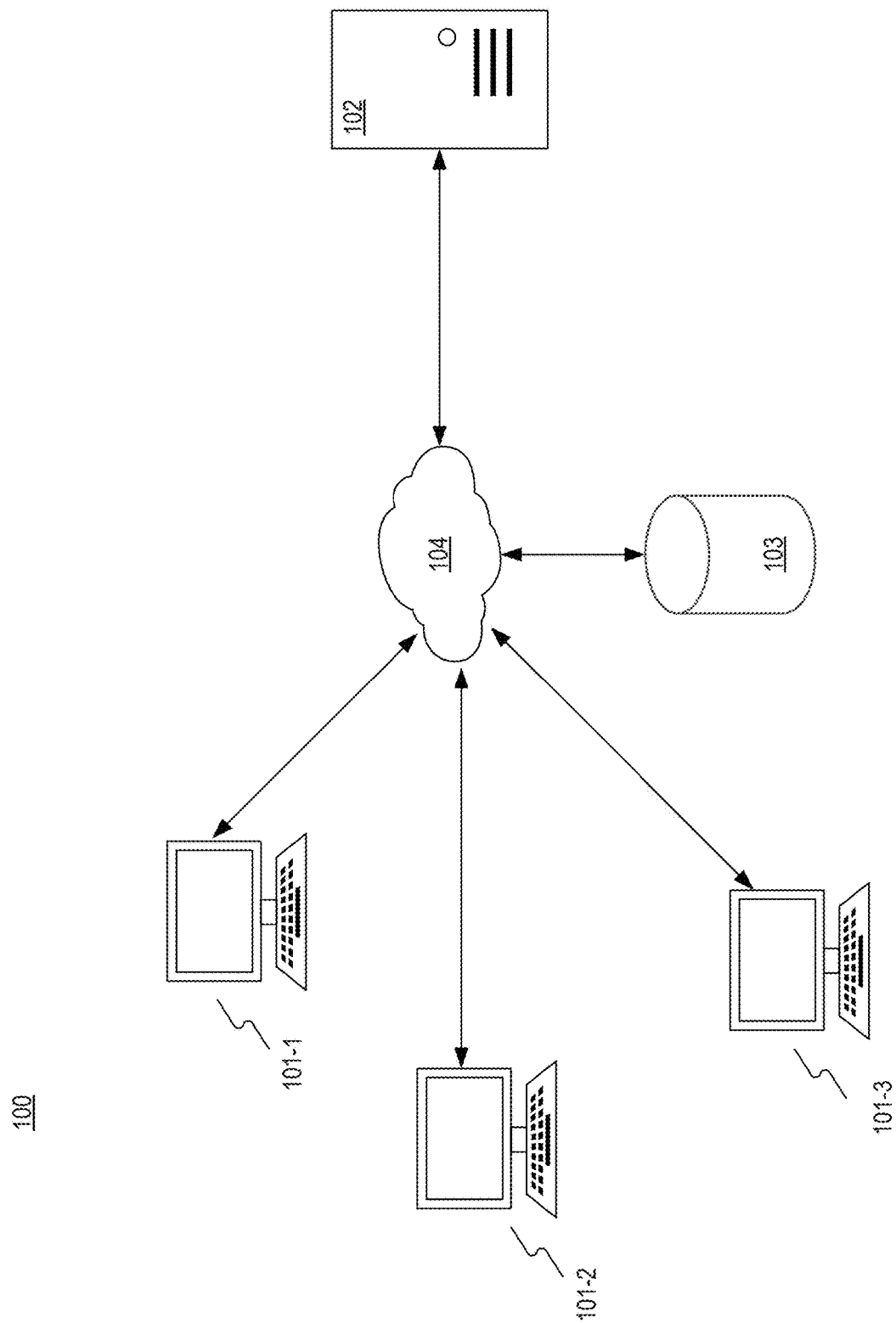
FIG. 1 is a diagram illustrating an exemplary system for analyzing patient parameter values, consistent with the present disclosure.

The following detailed description refers to the accompanying drawings. Wherever possible, the same reference numbers are used in the drawings and the following description to refer to the same or similar parts. While several illustrative embodiments are described herein, modifications, adaptations and other implementations are possible. For example, substitutions, additions, or modifications may be made to the components illustrated in the drawings, and the illustrative methods described herein may be modified by substituting, reordering, removing, repeating, or adding steps to the disclosed methods. Moreover, any of the steps in the illustrative methods may be performed consecutively or simultaneously. Accordingly, the following detailed description is not limited to the disclosed embodiments and examples. Instead, the proper scope is defined by the appended claims.

Embodiments herein include computer-implemented methods, tangible non-transitory computer-readable mediums, and systems. The computer-implemented methods may be executed, for example, by at least one processor (e.g., a processing device) that receives instructions from a non-transitory computer-readable storage medium. Similarly, systems consistent with the present disclosure may include at least one processor (e.g., a processing device) and a memory, and the memory may be a non-transitory computer-readable storage medium. As used herein, a non-transitory computer-readable storage medium refers to any type of physical memory on which information or data readable by at least one processor may be stored. Examples include random access memory (RAM), read-only memory (ROM), volatile memory, non-volatile memory, hard drives, compact disc (CD) ROMs, digital optical discs (DVDs), flash drives, disks, and any other known physical storage medium. Singular terms, such as "memory" and "computer-readable storage medium," may additionally refer to multiple structures, such a plurality of memories and/or computer-readable storage mediums. As referred to herein, a "memory" may comprise any type of computer-readable storage medium unless otherwise specified. A computer-readable storage medium may store instructions for execution by at least one processor, including instructions for causing the processor to perform steps or stages consistent with an embodiment herein. Additionally, one or more computer-readable storage mediums may be utilized in implementing a computer-implemented method. The term "computer-readable storage medium" should be understood to include tangible items and exclude carrier waves and transient signals.

A system for classifying patient information is disclosed. Aspects of the system may receive patient information and determine whether the patient information includes predicted anomalies. In some cases, such anomalies may be confirmed or rejected by a user, and the system may learn over time to improve its predictions. By enabling anomaly detection through analysis of current and historical information, more accurate patient information is delivered to requesters.

FIG. 1 illustrates an exemplary system 100 for implementing embodiments consistent with the present disclosure, described in detail below. As shown in FIG. 1, system 100 may include one or more client devices 101, a computing device 102, a database 103, and a network 104. It will be appreciated from this disclosure that the number and arrangement of these components are exemplary and provided for purposes of illustration. Other arrangements and numbers of components may be used without departing from the teachings and embodiments of the present disclosure.

A client device 101 (e.g., client device 101-1, 101-2, 101-3) may be configured to receive user input from a user for transmitting, classifying, validating, and/or transmitting patient information. For example, client device 101 may reside at a clinic, and a user (e.g., a physician or administrator) may enter information for creating new patient data at an input device (such as an input device 153) of client device 101. As another example, client device 101 may reside at a data analysis entity, which may receive patient information (e.g., from a client device at a clinic) and which may classify, validate, or otherwise analyze patient information (e.g., before transmitting information to a researcher, which may be associated with another client device 101). Client device 101 may include a processor, memory, input device, output device, or other computing component. For example, client device 101 may have components corresponding to those of computing device 102. By way of example, the user may enter an identification number at an interface of client device 101 for accessing patient information, and client device 101 may transmit the identification number to computing device 102. Computing device 102 may access, analyze, and or request patient information based on the identification number. Client device 101 may also receive and present information received from computing device 102. For example, client device 101 may receive information relating to one or more patients from computing device 102 and present the information at an interface of client device 101 to the user. In some embodiments, client devices 101-1, 101-2, and 101-2 may reside at the same site or different sites.

Computing device 102 may be configured to receive information from client device 101 for analyzing, classifying, transmitting, and/or otherwise manipulating patient information. In some embodiments, this information may be received directly from client device 101. For example, if client device 101 is included in a clinician's office, a doctor, nurse, assistant, or other representative of the clinician's office may input or otherwise collect the information and transmit it to computing device 102 via client device 101. In some embodiments, one or more additional systems may be involved in generation of the information that is received at computing device 102. For example, an intermediate system (not shown in FIG. 1) may compile and/or generate data included in the information received by computing device 102.

The patient information received by computing device 102 may include a variety of parameters related to a patient. As used herein, a patient parameter may include any value or property associated with a patient. In some embodiments, the patient parameter may include demographic data such as an age, race, ethnicity, gender, or the like. Alternatively, or additionally, the patient parameter may be associated with the health or medical treatment of a patient. For example, these parameters may include a testing status, a biomarker status, a medical condition, a trial status, a disease, a trial line of therapy, a genomic testing condition, one or more trial eligibility criteria for determining whether a patient is eligible for a trial, and/or other medical information related to a patient. Computing device 102 may further automatically generate an algorithm for determining a likelihood of whether patient data is anomalous. For example, computing device 102 may automatically generate an algorithm representing an expression tree, which may be based on analysis (e.g., statistical analysis) of patient information, and the nodes and/or leaves of the expression tree may represent classification and/or anomaly detection criteria. In some embodiments, a strength of likelihood of an anomaly may be determined, which may be based on past patient information, user inputs, and/or thresholds (e.g., statistical thresholds). For example, a set of patient information that is associated with a value (e.g., statistical metric) that is two standards of deviation away from a reference value (e.g., a median) may have a higher likelihood of being anomalous than a set of patient information that is associated with a value that that is one standard of deviation away from the reference value. Of course, an anomaly associated with a value may also be associated with data underlying the value (e.g., underlying data giving rise to an anomalous standard deviation value). In some embodiments, a likelihood of anomaly and/or other analysis information may be stored and/or transmitted by a client device 101, a computing device 102, and/or any other device suitable for managing patient data.

Computing device 102 may also be configured to obtain electronic records associated with a plurality of patients and parse the records to generate data for analysis, aggregation, classification, verification, etc. For example, computing device 102 may obtain electronic records associated with the patients of a clinic (e.g., a clinic associated with client device 101). Additionally, client device 101 and/or computing device 102 may be configured to receive and/or process input information for a model. For example, client device 101 may include or may be connected to a scanning device, which may scan documents (e.g., documents containing unstructured data) associated with a patient. For example, a scanning device (e.g., a portable document scanner) may scan a handwritten note from a doctor and convert it to an image or other data entity (e.g., structured data). Computing device 102 may determine new information for a patient based on an algorithm and electronic records. By way of example, computing device 102 may create a namedtuple that has numbers and a series of letters for each of the patients based on the electronic record (e.g., age, disease, biomarkers). Computing device 102 may evaluate the created namedtuples associated with the patients against an expression tree, which may return result of derived data for the patients. The new information may be determined based on structured and/or unstructured data in the record. Structured data may include quantifiable or classifiable data about the patient, such as gender, age, race, weight, vital signs, lab results, date of diagnosis, diagnosis type, disease staging (e.g., billing codes), therapy timing, procedures performed, visit date, practice type, insurance carrier and start date, medication orders, medication administrations, or any other measurable data about the patient. Unstructured data may include information about the patient that is not quantifiable or easily classified, such as physician's notes or the patient's lab reports. Unstructured data may be represented as typed or handwritten text, such as a physician's description of a treatment plan, notes describing what happened at a visit, statements or accounts from a patient, subjective evaluations or descriptions of a patient's well-being, radiology reports, pathology reports, laboratory reports, etc.

Computing device 102 may further be configured to analyze (e.g., according to a model, algorithm, user parameter, etc.) patient information to predict whether patient information is anomalous. For example, computing device 102 may analyze patient information with respect to a reference expression (e.g., a value associated with prior data, such as a median value, mean value, difference value, trend value, equation of best fit, etc.), and may output analysis results to an output device (e.g., a display, printer). Alternatively or additionally, computing device 102 may transmit instructions for displaying information representing the analysis to client device 101, which may present the information to the user.

In some embodiments, computing device 102 may be configured to provide analyses for one or more patient information datasets and/or one or more possible anomalies. For example, the user may select a number of datasets and/or patient parameters to analyze at a client device 101 and computing device 102 may determine one or more likelihoods of anomalies (e.g., anomalies for different patient parameters, different datasets, different time periods, etc.), which may be based on one or more anomaly algorithms and the electronic record associated with at least one patient. Additional details regarding the detection anomalies by computing device 102 are provided below.

In some embodiments, client device 101 and computing device 102 may be integrated into one device configured to perform the functions of client device 101 and computing device 102 disclosed herein. For example, a user may input information for displaying patient and/or anomaly information via input device 153 of computing device 102, which may display one or more possibly anomalies via an output device (e.g., output device 154, discussed below).

Database 103 may be configured to store information and data for one or more components of system 100. For example, database 103 may store electronic records associated with one or more patients. Database 103 may also store information relating to one or more patients. For example, database 103 may store patient testing statuses, biomarker statuses, etc. In some embodiments, database 103 may also store algorithms and/or models for analyzing patient information, such as determining possible patient information anomalies. Client device 101 and/or computing device 102 may be configured to access and obtain the data stored on database 103 via network 104. In some embodiments, database 103 may be operated by a third party. For example, computing device 102 may request information relating to a particular patient or set of patients from database 103, which may transmit the requested information to computing device 102. By way of example, computing device 102 may request the information by transmitting a patient identifier, patient group identifier, medical organization identifier, etc. to database 103, which may transmit the requested information (e.g., patient testing status) to computing device 102.

Network 104 may be configured to facilitate communications among the components of system 100. Network 104 may include a local area network (LAN), a wide area network (WAN), portions of the Internet, an intranet, a cellular network, a short-ranged network (e.g., a Bluetooth™ based network), or the like, or a combination thereof.

Figure 2:
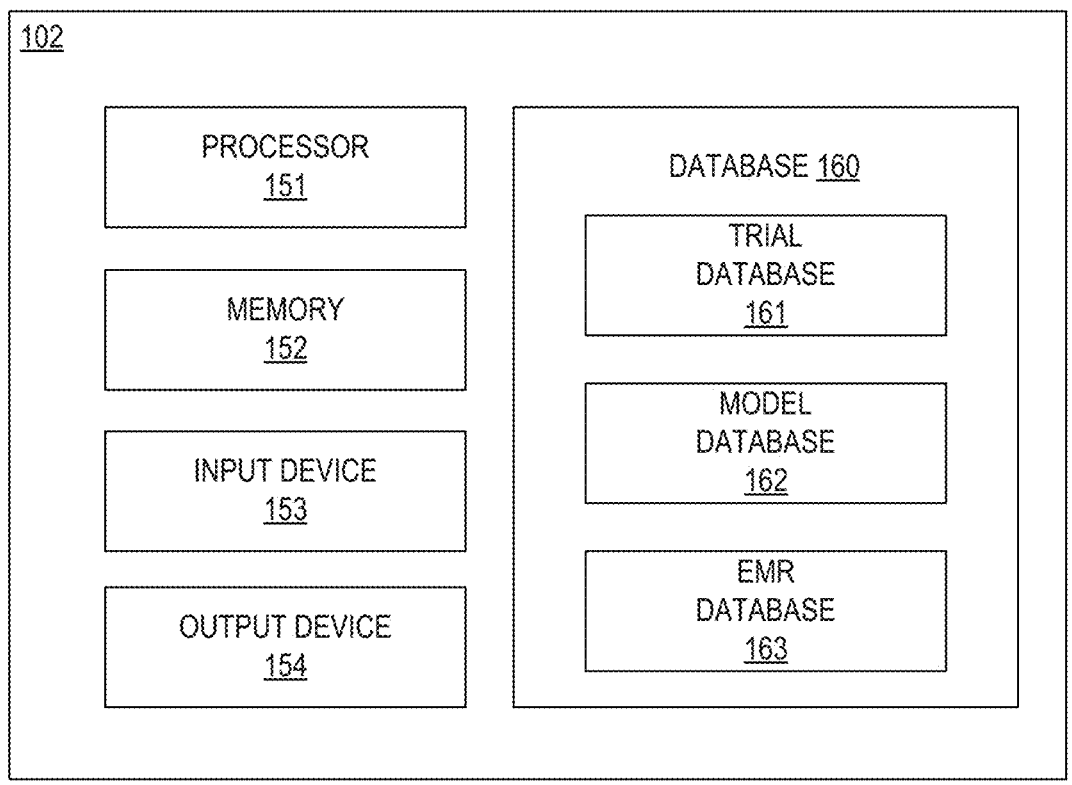
FIG. 2 is a diagram illustrating an exemplary computing device for analyzing patient parameter values, consistent with the present disclosure.

FIG. 2 is a block diagram illustrating an exemplary computing device 102. Computing device 102 may include at least one processor (e.g., processor 151), a memory 152, an input device 153, an output device 154, and a database 160.

Processor 151 may be configured to perform one or more functions described in this disclosure. As mentioned, computing device 102 may include memory 152 that may store instructions for various components of computing device 102. For example, memory 152 may store instructions that, when executed by processor 151, may be configured to cause processor 151 to perform one or more functions described herein.

Input device 153 may be configured to receive input from the user of computing device 102, and one or more components of computing device 102 may perform one or more functions in response to the input received. In some embodiments, input device 153 may include a touchscreen, a keyboard, a microphone, a speaker, a haptic device, a camera, a button, a dial, a switch, a knob, a touch pad, a button, a microphone, a location sensor, an accelerometer, a camera, a fingerprint scanner, a retinal scanner, a biometric input device, an ultrasonic scanner, a transceiver, an input device, an output device, or other input device to perform methods of the disclosed embodiments. For example, input device 153 may include an interface displayed on a touchscreen (e.g., output device 154). Output device 154 may be configured to output information and/or data to the user. For example, output device 154 may include a display configured to display one or more suggested patients for a trial (e.g., a light-emitting diode (LED) display, a liquid crystal display (LCD) display, etc.). In some embodiments, output device 154 may include a touchscreen.

Database 160 may be configured to store various information for one or more components of computing device 102. For example, database 160 may include a trial database 161, a model database 162, and an electronic medical record (EMR) database 163. Trial database 161 may be configured to store information relating to one or more trials, including trial eligibility criteria. A trial may include, without limitation, a patient testing trial, a drug trial, a medical procedure trial, and/or any other trial related to the health of patients. Trial database 161 may further store edit history including changes made to a trial. Computing device 102 may obtain information relating to the trials from trial database 161 and modify the information if needed. For example, computing device 102 may create a trial portfolio for a new trial (e.g., a data structure for patient information associated with the trial) and store the trial portfolio into trial database 161.

Model database 162 may store patient information analysis models or algorithms. A patient information analysis algorithm refers to an algorithm for analyzing patient information (e.g., patient data), such as by determining a likelihood of whether patient data is anomalous. Computing device 102 may obtain algorithms from model database 162. In some embodiments, computing device 102 may create an algorithm and store the created algorithm into model database 162. A patient information analysis model may be configured to determine various aspects of patient information, such as determining a degree of closeness between patient information and a reference expression, determining a degree of closeness between two sets of patient data, determining a likelihood of a patient information anomaly, etc. A model may be configured to perform this analysis according to any number of user-configurable and/or machine-configurable parameters (e.g., weights, coefficients, hyperparameters, etc. that may influence model operations). A model may be, without limitation, any one of a computer software module, an algorithm, a machine learning model, a data model, a statistical model, a recurrent neural network (RNN) model, a long-short term memory (LSTM) model, or another neural network model, consistent with the disclosed embodiments. A model may be trained or untrained, and may be supervised or unsupervised. The parameters and/or algorithms stored in model database 162 may be used to detect anomalies in patient data sets, as described further below. For example, computing device 102 may receive data from computing device 101 (either directly or indirectly), database 103, and/or other sources, and may analyze the data using models defined by model database 162. Computing device 102 may further update these model parameters or other information in model database 162 based on feedback from a user.

EMR database 163 may store electronic medical records associated with patients, which may contain structured and/or unstructured patient information (e.g., a patient testing condition, disease, etc.). Processor 151 may receive one or more electronic medical records from EMR database 163. In some embodiments, EMR database 163 may be omitted. For example, rather than storing electronic medical records within computing device 102, processor 151 may be configured to access database 103 or computing device 101 to receive and analyze patient medical records. In some embodiments, EMR database 163 may temporarily store the electronic medical records.

While FIG. 2 illustrates database 160 as having three separate components (trial database 161, model database 162, and EMR database 163) for illustration purposes, it is to be understood that two or more of these databases may be combined into a single database. For example, computing device 102 may include a single database 160 including some or all of the data represented by trial database 161, model database 162, and EMR database 163. Further, in some embodiments, the data stored in one or more of these databases may be stored in a different location, for example, in memory 152, database 103, a cloud-storage device, a remote server, or the like.

As discussed above, computing device 102 may determine a likelihood of an anomaly of patient information based on a patient information algorithm, electronic medical records of a patient, patient information statistics, and/or user input. For example, computing device 102 may use processor 151 to determine one or more predicted anomalies (e.g., of patient data) related to at least one patient parameter. In some embodiments this may include tracking values for the patient parameter over time. For example, computing device 102 may receive data from computing device 101 and/or database 103, as described above. Computing device 102 may analyze the data and store the data for future analysis. For example, the data may be stored in database 160, memory 152, or various other storage locations. When new or additional data is received, computing device 102 may retrieve the stored parameter values and compare new parameters values to the retrieved values, which may provide insight on whether variations in the parameters are anomalous, or merely reflect normal variations in data. In some embodiments, this may include comparing the current parameters indicated in the new or additional data with the stored historical parameters to identify changes or trends that may indicate an anomaly. In some embodiments, the historical parameters may be analyzed over time (e.g., parameters collected over several sets of data) to track statistical fluctuations in the data, as described further below.

As an illustrative example, computing device 102 may be configured to analyze data including test scores for a particular biomarker (e.g., PDL1) for a particular patient or group of patients. An abnormally high biomarker score, for example, may indicate an anomaly in the dataset analyzed by computing device 102. However, based on analyzing previous datasets retrieved by computing device 102, the high biomarker score may be attributed to the patient's condition, rather than an error with the dataset. For example, if looking at the biomarker PDL1, the patient may exhibit a trend in gradually increasing PDL1 scores over time which may indicate that the heightened value is not an anomaly. Conversely, the current dataset may show a PDL1 value within a normal range, where analysis of previous datasets may indicate an anomaly. For example, a patient may have consistent test scores at a particular value and the current value, while within an acceptable range, may be abnormal for this patient. Accordingly, the system may flag the current score as a potential anomaly.

This analysis of past values may occur in a variety of ways. In some embodiments, computing device may compare a difference between the current value and a previous value to a threshold. If the second value differs from the previous value by more than the threshold amount, the parameter may be flagged as potentially anomalous. This threshold may be determined in a variety of ways. In some embodiments, the threshold may be a default value stored in the system (e.g., in database 162). In some embodiments, the threshold may be set by a user, such as an administrator. Each parameter may have its own associated threshold, or one threshold may apply to all parameters, a group or subset of parameters (e.g., based on type of parameter, etc.), a particular patient or group of patients, or the like. In some embodiments, the thresholds may be dependent on other factors. For example, the system may observe trends in data that are cyclical. Accordingly, the threshold may also vary cyclically (e.g., based on a time of year), such that the parameters considered to be potentially anomalous also varies.

Further, a trend may not necessarily be analyzed with respect to one particular patient or one particular patient parameter, and such analysis may be done at various levels of granularity. For example, the analysis of past values may include analyzing trends associated with multiple parameters over varying ranges of time. Further, trends may be analyzed with respect to more than one patient, such as a trend occurring within a group of patients having similar conditions, treatment plans, diagnoses, or the like. The trend associated with the group of patients may indicate an anomaly associated with one or more of the patients in the group. The data may be grouped and analyzed in various other ways. In some embodiments, data may be grouped in reference to particular timeframes. For example, the system may analyze a group of data occurring before or after the occurrence of a particular event. Example events may include the introduction of a new site that provides data for a patient, a change in medical providers for a patient, or any other event of interest.

In some embodiments, the system may analyze several previous data sets (i.e., historical data) to detect the anomalies. Accordingly, the current parameter value may be compared to a statistical value from the historical data. For example, this may include determining one or more of an average value (e.g., a mean, a median, a mode, a rolling average, geometric mean, a harmonic mean, etc.), a standard deviation, or the like. As one example, computing device 102 may determine whether the current value differs from a rolling average of the value by more than a threshold amount and, if so, flag the value as potentially anomalous. In another example, computing system 102 may determine whether the current value differs from the previous values by more than a standard deviation. While various examples are provided throughout the present disclosure, a person of skill in the art would appreciate additional statistical analysis techniques may be performed to detect the anomalies.

In some embodiments, computing device 102 may use a trained machine learning model to detect anomalies. For example, an artificial neural network may be trained using training data including one or more current data sets, each being associated with one or more historical data sets representing data captured prior to the current data sets, where various parameters in the current data sets are associated with an indication of whether the parameter is anomalous. This training data may be input into the model to develop a trained model configured to analyze additional data sets to detect these anomalies. In some embodiments, the training data set maybe manufactured (either manually or through an automated process). For example, a series of data sets may be retrieved and in a most recent data set, various parameters may be artificially altered and flagged as anomalies. Accordingly, the trained model may be configured to detect these anomalous values. While an artificial neural network is described by way of example, various other machine learning algorithms may be used. For example, the model may include one or more of a logistic regression, a linear regression, a regression, a random forest, a K-Nearest Neighbor (KNN) model (for example as described above), a K-Means model, a decision tree, a cox proportional hazards regression model, a Naïve Bayes model, a Support Vector Machines (SVM) model, a gradient boosting algorithm, or any other form of machine learning model or algorithm. Alternatively, or additionally, an unsupervised machine learning algorithm may be used to detect anomalies. The unsupervised algorithm may be configured to detect patterns from data. Accordingly, rather than being presented with a training data set with data tagged as anomalous, the machine learning algorithm may attempt to mimic training data that is provided and may use an output to correct itself. For example, the model may be provided with a score or numerical indicator of its performance (e.g., as a reinforcement learning process). As another example, the algorithm may be a semi-supervised model in which a relatively small portion of data is tagged.

Figure 3:
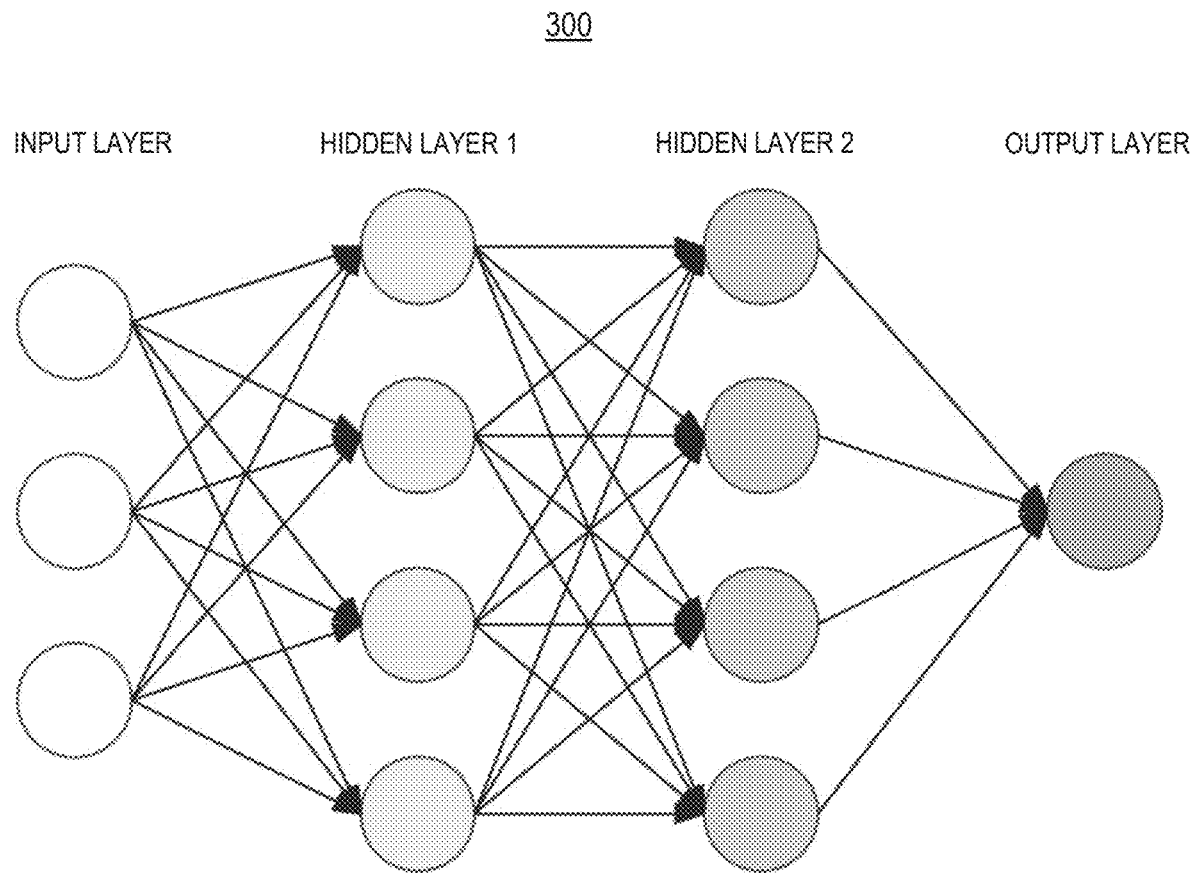
FIG. 3 is a diagram illustrating an exemplary neural network for analyzing patient parameter values, consistent with the present disclosure.

FIG. 3 illustrates an example neural network 300 that may be used for detecting anomalies, consistent with the disclosed embodiments. Neural network 300 may include an input layer, one or more hidden layers, and an output layer. Each of the layers may include one or more nodes. In some embodiments, the output layer may include one node. Alternatively, the output layer may include a plurality of nodes, and each of the nodes may output data (e.g., a prediction based on patient information). The model parameters associated with the nodes may be stored in model database 162, as described above. The input layer may be configured to receive input comprising a current data set of patient parameters and one or more previous data sets including these parameters. In some embodiments, every node in one layer may be connected to every other node in the next layer. A node may take the weighted sum of its inputs and pass the weighted sum through a non-linear activation function, the results of which may be output as the input of another node in the next layer. The data may flow from left to right, and the final output may be calculated at the output layer based on the calculation of all the nodes. As a result, neural network 300 may generate an output comprising an indication of whether the input values indicate an anomaly, as described above.

Alternatively, or additionally, anomalous values may be detected based on one or more rules. For example, a threshold for a particular value may be defined such that if the value exceeds (or falls below) the threshold value, the value may represent an anomaly. Various other forms of threshold may be defined and used to detect anomalies. For example, a threshold may relate to a rate of change of a particular value, a length of time during which a value remains unchanged (or within a particular range, etc.), a frequency at which data is collected, or other characteristics or properties of patient parameter data. These rules (and/or thresholds) may be defined in various ways. For example, a user (such as an administrator) may define rules for detecting anomalies through a user interface of client device 101, computing device 102, or another device associated with system 100. As another example, the rules or threshold values may be predefined values, such as default values, values defined by a company or organization, values defined according to a scheme or set of rules, or the like. In some embodiments, the rules may be determined based on the results of a machine learning algorithm, such as neural network 300 described above. Accordingly, the neural network may not be implemented each time but may be used to establish a set of rules or threshold values.

According to some embodiments, computing device 102 may only surface parameters flagged as potentially anomalous to a user of the system. In other words, computing device 102 may perform an automated analysis to filter parameter values that are most likely to represent an anomaly. These flagged parameter values may then be presented to a user, for example, through a graphical user interface. Various graphical interfaces are described below with respect to FIGS. 4A, 4B, 5A, 5B, 5C, 6A, and 6B. Accordingly, the amount of data a human inspector may be required to review may be greatly reduced. In particular, rather than the human user having to review thousands of pages of reported parameter variations, only a subset of parameters most likely to represent an anomaly may be presented to the user. The system may also display one or more historical values, as well as reasons for why the data was flagged as potentially anomalous, as shown in FIG. 6B and described below. Further, the automated system may be able to detect anomalies that may be imperceivable to a human user, for example, through the use of a trained machine learning model. Accordingly, this automated analysis may greatly improve the efficiency and accuracy of the review process.

Computing device 102 may also generate a data structure (e.g., a linked list, a self-referential table, an extensible markup language (XML) file, etc.) representing the relationship between the patient information and predicted and/or verified anomalies and store the data structure in a database (e.g., database 103, database 160). Computing device 102 may further present the data representing the relationship between the patient information and anomaly (or anomalies) to the user. For example, computing device 102 may be configured to generate an anomaly report. By way of example, computing device 102 may receive user input for defining filters for the data to appear on the report, including, for example, patient information (e.g., gender, age, location, patient schedule, diagnosis, biomarker, predicted testing condition, verified testing condition, or the like, or a combination thereof), treatment information (e.g., treatment, inclusionary and/or exclusionary drug), and trial information (trial name, study drug, sponsor, study type, trial description, diagnosis, biomarker criteria, line of therapy, or the like, or a combination thereof).

In some embodiments, computing device 102 may receive, through a user interface, user inputs confirming or dismissing the potential anomalies. For example, each of the parameters flagged as representing a potential anomaly may be displayed on a graphical user interface (as shown, for example, in FIGS. 6A and 6B and described below). A human user may review each of the potential anomalies and may either confirm them as anomalous or dismiss them, indicating they represent valid or expected parameters. Computing device 102 may be configured to take a responsive action based on parameters confirmed as anomalous. For example, this may include generating an alert, omitting the parameter from the data set, flagging the parameter for investigation, or various other actions. In some embodiments, computing system 102 may further be configured to improve the model used to determine the anomalies based on the feedback for the user. For example, this may include modifying a threshold used to detect anomalies or modifying model parameters (e.g., weights, etc.) for a machine learning model. Accordingly, the prediction accuracies may improve over time, which may further improve the accuracy and efficiency of the system.

FIGS. 4A, 4B, 5A, 5B, 5C, 6A, and 6B illustrate exemplary user interfaces for analyzing patient information, consistent with the present disclosure. Any of the exemplary user interfaces described herein may be displayed via output device 154 of computing device 102 (e.g., a display or touchscreen), and the user may enter information via input device 153. Alternatively or additionally, computing device 102 may transmit instructions to client device 101 for displaying a user interface via an output device of client device 101 (e.g., a display or touchscreen) and for receiving user input via an input device of client device 101. For example, client device 101 may be associated with a researcher, that may be configured to provide input regarding potential anomalies in the data. The user interfaces provided in FIGS. 4A, 4B, 5A, 5B, 5C, 6A, and 6B are provided by way of example. It is to be understood that one or more elements of these interfaces may be modified and/or omitted. Moreover, any aspect of a user interface shown in one user interface may be removed, modified, and/or combined with an aspect of another user interface. For example, a search bar of one user interface may also be included as part of another user interface.

Exemplary FIG. 4A illustrates an exemplary user interface 400A for patient information. User interface 400A may include a number of graphical elements, which may be user-interactable, non-interactable, or a combination of both. For example, user interface 400A may display patient information including numbers and percentage of patients associated with different cancer group stages (e.g., Stages I, IA, IB, II, IIA, IIB). Information displayed at user interface 400A (which may be displayed in a display frame 420) may be determined, at least in part, by user selection of buttons or other graphical elements included in a selection frame 410 of interface 400A, which may cause the display of information related to patients. Accordingly, interface 400A may be configured to enable a user to select information related to a particular patient parameter. For example, selection frame 410 may include a cancer group stage button 411, a comorbidities button 412, a cardiac dysfunction button 413, additional malignancies button 414, menopausal status button 415, and/or biomarker status button 416, which may allow a user to filter based on the selected information. Other example parameters may include a cancer status or other disease status, real-world progression, real-world response, real-world adverse effect, and/or any other indicator of a patient parameter associated with at least one patient, as discussed herein. For example, information related to patients having indicators of a testing status (e.g., tested, untested, unknown, etc.) may be displayed. Of course, combinations of patient parameters may be selected, such that patient information related to patients having, for example, both a diabetic status and a biomarker status, may be displayed. In some embodiments, user interface 400A may display information related to a plurality of patients in a group of rows, a group of columns, a chart, a graph, a table, an animation, or other visual format for displaying data. Such data may be searchable (e.g., using the search bar shown in FIG. 4A) and/or navigable (e.g., using the page, previous, and/or next indicators near the bottom right of exemplary user interface 400A) by a user. User interface 400A may also include interactable graphical elements for filtering and/or ordering data (e.g., for ordering rows based on a highest-to-lowest percentage for a patient parameter, a lowest-to-highest percentage for a patient parameter, a newest-to-oldest age of data, etc.).

Exemplary FIG. 4B illustrates an exemplary user interface 400B for patient information. Like user interface 400A, user interface 400B may include a number of graphical elements, which may be user-interactable, non-interactable, or a combination of both. For example, user interface 400A may include a display frame 440 showing patient information 442 and 444, each including numbers of patients or percentage of patients associated with testing statuses for different timeframes. Information displayed at user interface 400B may be determined, at least in part, by user selection of buttons 432 and 434 in selection frame 430 or other graphical elements, which may cause the display of information related to patients associated with a particular patient parameter and/or timeframe (e.g., a date, day, month, year, or other indication of a point in time or a period of time). For example, information related to patients having indicators of a testing status (e.g., tested, untested, unknown, etc.) at a particular time (e.g., February 2018) may be displayed. Of course, as with user interface 400A, combinations of patient parameters may be selected. In some embodiments, user interface 400B may display information related to a plurality of patients in a group of rows, a group of columns, a chart, a graph, a table, an animation, or other visual format for displaying data. Such data may be searchable (e.g., using search bar 454 shown in FIG. 4B) and/or navigable (e.g., using the page, previous, and/or next indicators 452 shown near the bottom right of exemplary user interface 400B) by a user. User interface 400B may also include interactable graphical elements for filtering and/or ordering data (e.g., for filtering data to only display patient information associated with particular dates and/or timeframes).

In some embodiments, the analysis to detect potential anomalies in the data maybe automatic and may apply to all parameters in a data set. However, in some embodiments, various aspects of the analysis may be based on input from the user. For example, the user may select one or more parameters within a data set for analysis by computing system 102. This may include, filtering the data set, searching the data set, selecting individual parameters from the data set, or other means of narrowing a data set for analysis. The user may then submit this selection, for example, by clicking a "Run Analysis" button on a selected group of parameters.

Exemplary FIG. 5A illustrates a user interface 500A for a patient data report. In some embodiments, user interface may be generated in response to a user request. For example, a user may select a cohort identifier, a disease, and/or any combination of patient parameters discussed herein, and a device (e.g., computing device 102) may generate a corresponding report. For example, a device may generate a number of data elements (shown in exemplary fashion as rows in FIG. 5A), which may be associated with a cohort, patient, and/or clinic. A data element may describe one or more patient parameters such as a disease identifier or a section (e.g., a section of patients for a test). A data element may also include a generated value, such as an absolute difference (e.g., between a patient information values, discussed further below), a statistical value, a threshold, a likelihood of an anomaly, or the like. In some embodiments, data elements may be filterable and/or orderable by a patient parameter and/or associated value (e.g., test variable, absolute difference between datasets, etc.). In some embodiments, certain graphical elements may be displayed with a particular color, shading, pattern, animation, bold text, or other visual indicator to emphasize information associated with the graphical element. For example, a graphical element associated with a threshold, comparison (e.g., a comparison of a data value to a threshold), or other analytical expression and/or value may have a color that indicates a connection between the information associated with the graphical element and a likelihood of a patient information anomaly. By way of further example, graphical elements indicating that an absolute difference between two values (e.g., two medians of two patient datasets) exceeds a threshold (e.g., 5%) may be displayed using a red color. In some embodiments, one portion of user interface 500A may include alerts associated with patient information (e.g., an alert indicating a potential anomaly, an alert indicating a lack of sufficient data to make a prediction based on a sufficiency criterion, etc.) and another portion may include a number of changes to patient parameters of a group of patients (e.g., a cohort). In some embodiments, user interface 500A, or any other user interface, may display data from multiple entities (e.g., medical organizations), allowing for comparison across data sources. In some embodiments, indicators may be placed on data associated with one entity whose dataset differs from another dataset (e.g., of another entity) by a predetermined threshold (e.g., has a difference in median values that exceeds a threshold).

Figure 5B:
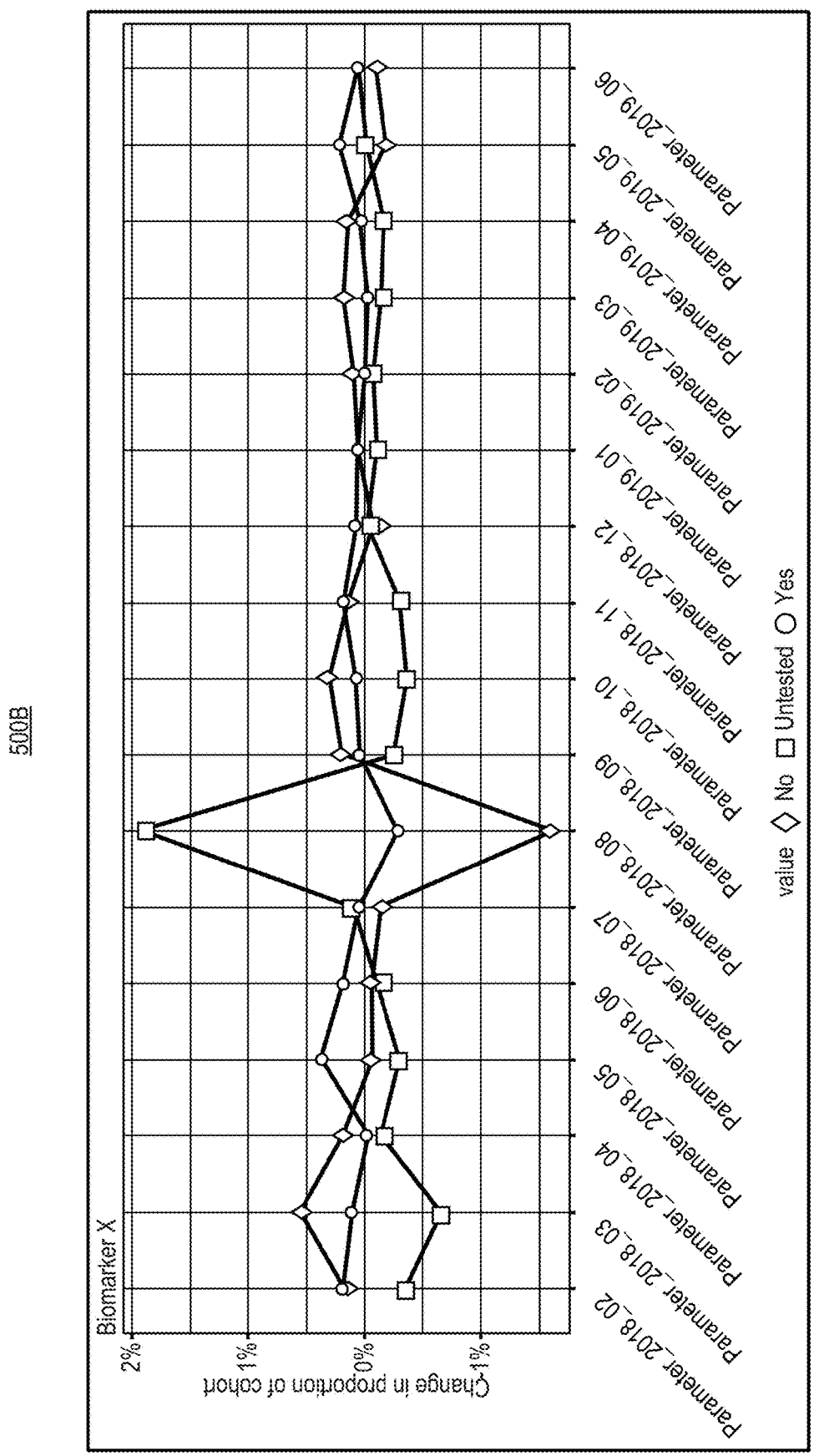

Exemplary FIG. 5B illustrates a first patient information graph 500B, which may depict data associated with a patient or a plurality of patients. In some embodiments, first patient information graph 500B may be displayed in response to a user input at a user interface (e.g., a selection of a graphical element causing a computing device 102 to generate a graph of patient information). In some embodiments, first patient information graph 500B may display a degree of change of a patient parameter (e.g., for a cohort) over a period of time (e.g., days, weeks, months, etc.). For example, first patient information graph 500B may display a degree of change for different cohorts of patients within the same graph. In the example shown in FIG. 5B, degrees of change for patient parameters associated with a testing status for a group of patients are shown, though, either additionally or alternatively, changes associated with other patient parameters may be shown, consistent with disclosed embodiments. In some embodiments, an alert box, color, warning symbol, or other indicator may be displayed to show a data point or group of data points that is associated with a predicted and/or verified anomaly. In some embodiments, a data point or line (e.g., as shown in FIG. 5B) may have an area of colored shading around it (e.g., different from the color of the point and/or line as well as the background of a graph), which may indicate an acceptable degree of deviation (e.g., one standard deviation away from the point and/or line), which may be based on a computerized model and/or user input. In some embodiments, a user may toggle a selection of an indicator (e.g., an indicator associated with a graph's key, as shown near the bottom of FIG. 5C), which may cause data to be displayed or removed from first patient information graph 500B.

Figure 5C:
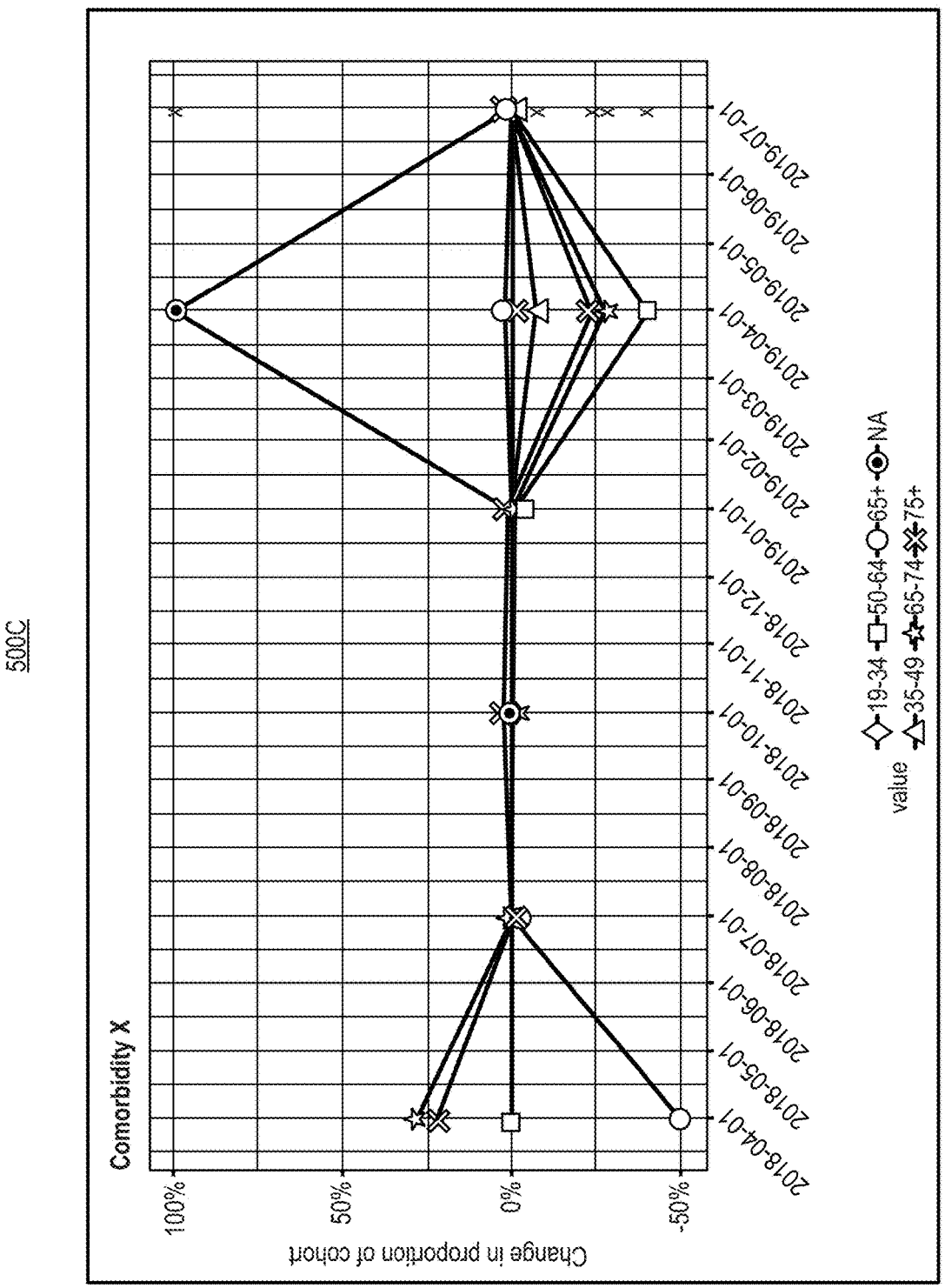
Figure 6B:
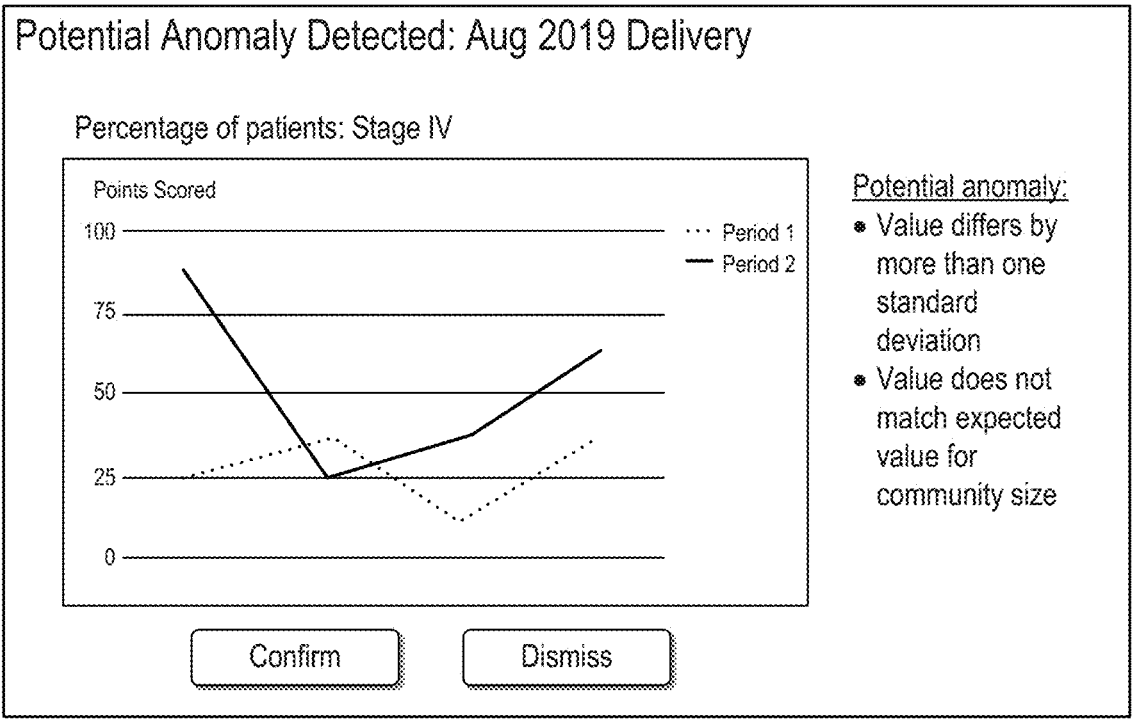

Exemplary FIG. 5C illustrates a second patient information graph 500C, which may depict data associated with a patient or plurality of patients. In some embodiments, second patient information graph 500C may display a degree of change of a patient parameter (e.g., a change in a number of patients within a particular group or cohort). For example, second patient information graph 500C may display degrees of changes in the number of patients in multiple cohorts, with multiple cohorts represented as points and/or lines. Second patient information graph 500C may also include any or all of the features of first patient information graph 500B.

Exemplary FIG. 6A illustrates an example user interface 600A, which may be associated with information related to predicted and/or verified anomalies. For example, user interface 600A may include patient information anomalies predicted by a model and/or verified by a user. A patient information anomaly may be related to a particular group of patients, for example, a group of patients related to a patient parameter indicating they are associated with a myeloma condition. User interface 600A may include a reason related to a prediction of an anomaly. For example, user interface 600A may include an indication that a dataset has a value (e.g., mean, median, mean differential, median differential, etc.) that exceeds a threshold (e.g., a standard deviation away from a value of another dataset). Although not shown in FIG. 6A, in some embodiments, the user may be able to provide input through user interface 600A. For example, user interface 600A may allow a user to select one or more of the potential anomalies and mark them as confirmed or dismiss them. In some embodiments, the user may be able to select (e.g., by clicking, tapping, hovering over the item, etc.) one or more of the listed potential anomalies for additional information.

FIG. 6B illustrates an example user interface 600B for reviewing potential anomalies, consistent with the disclosed embodiments. User interface 600B may be presented, for example, through input device 153 and/or output device 154. In some embodiments, user interface 600B may be presented on a mobile device, such as a phone, tablet, or similar device. User interface 600B may display one or more potential anomalies listed in user interface 600A. In some embodiments, user interface 600B may show information that may help a user determine whether the value is anomalous or not. For example, this may include a graphical display area showing trends in one or more parameters over time. In some embodiments, this may include trends over a plurality of different time periods. User interface 600B may also include information indicating why the parameter was flagged as potentially anomalous. This may include an indication of a statistical variation associated with the parameter, text-based analysis for the parameter, or other information. A user may be able to provide feedback regarding the detected anomaly through user interface 600B. For example, as shown, a user may select "confirm" or "dismiss" to provide input regarding the potential anomaly. While input buttons are provided by way of example, it is to be understood that various other means of providing input may be implemented, for example, through a touch interface (e.g., swiping left to dismiss, swiping right to confirm, etc.), a speech-based interface, or the like.

Figure 7:
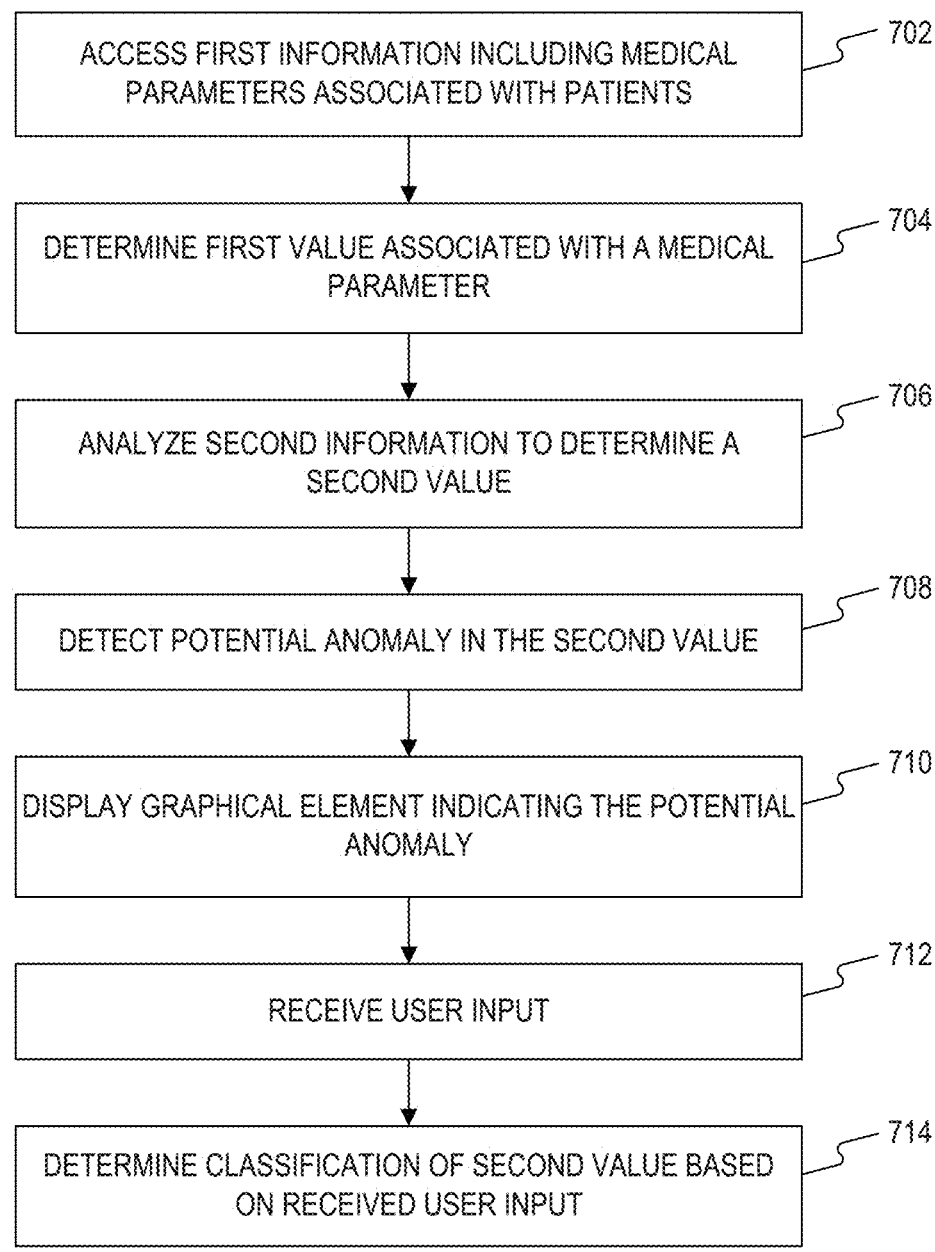
FIG. 7 is a flowchart illustrating an exemplary process for classifying patient information, consistent with the present disclosure.

FIG. 7 is a flowchart illustrating an exemplary process 700 for classifying patient parameter values, consistent with the present disclosure. While process 700 is described in connection with computing device 102 (e.g., using processor 151), one skilled in the art would understand that one or more steps of process 700 may be performed by other components of the system.

At step 702, computing device 102 may access first information associated with a plurality of patients. In some embodiments the first information may include a plurality of patient parameters associated with the plurality of patients. For example, the first information may include a plurality of patient datasets, which may contain patient identifiers (e.g., medical identification numbers, names, dates of births, etc.) and associated patient parameters. As described above, a patient parameter may include any value or property associated with a patient. In some embodiments, a patient parameter may include medical information, such as a testing status, a biomarker status, a trial status, a disease status, a section identifier, a cohort identifier, a clinic identifier, a medical organization identifier, a trial line of therapy, a patient age, a date, a time, a patient ethnicity, a patient gender, a genomic testing condition, a group stage, a degree of alcohol use, a diabetic status, an encephalopathy status, a hepatitis status, an obesity status, a biomarker status, a cancer status, a medical condition, one or more trial eligibility criteria for determining whether a patient is eligible for a trial, and/or other medical information related to a patient. Computing device 102 may access the first information in various ways. In some embodiments, computing device 102 receive the first information from a single entity (e.g., client device 101 associated with a clinic) or from multiple entities (e.g., multiple client devices 101). In some embodiments, client device 102 may receive the first information during a first time period (e.g., during a particular number of hours, days, weeks, months, and/or years, and/or during a particular study, testing effort, etc.). In some embodiments, computing device 102 may receive a plurality of historical values associated with a patient parameter. In some embodiments, computing device 102 may access the first information from a local data storage (e.g., memory 152), from a remote storage location (e.g., a remote server, a cloud storage platform, etc.) or other forms of storage devices. As described above, in some embodiments, one or more additional processes or systems may be involved in providing the first information to computing device 102. For example, an intermediate computing device may compile data from different sources (e.g., client devices 101) and may generate a data set to be provided to computing device 102.

At step 704, computing device 102 may determine a first value associated with a patient parameter of at least one of the plurality of patients. In some embodiments, the first value may be a value of the patient parameter (e.g., a date, test score, vital sign, etc.). In some embodiments, the first value may be a value determined directly from the first information (e.g., historical values of a group of patients). For example, the first value may be a mean or median of the plurality of values (e.g., historical values). In some embodiments, the first value may be a first difference between values generated from the plurality of historical values associated with a patient parameter. In some embodiments, the first value may be a first difference between derived values generated from a plurality of historical values associated with a patient parameter. For example, the first value may be a difference between a first mean (or other statistical value) of a first dataset and a second mean (or other statistical value) of a second dataset. In some embodiments, a difference may be described as a degree of change (e.g., a 5% change for a value within historical data, an average change over time of 3.5% for a value, etc.).

In some embodiments, computing device 102 may determine more than one value from patient information. For example, computing device 102 may determine a ranking of patient parameters based on the first information (e.g., a percent of patients that are of a particular race within the first information), and may generate percentiles based on the ranking. In some embodiments, computing device 102 may determine a relative distribution of a patient parameter among a group of patients (e.g., gender distribution, age distribution, race distribution, geographic distribution, etc.). As another example, computing device 102 may determine a value range, quartile, quintile, multiple means, multiple medians, multiple difference values, etc.

At step 706, computing device 102 may analyze second information associated with at least one patient to determine a second value of the patient parameter. As with the first information, the second information may be patient information (e.g., one or more patient data sets). In some embodiments, computing device 102 may receive the second information from a remote source. In some embodiments, computing device 102 may receive the second information during a second time period, where the first time period (e.g., associated with the first information, as discussed above) may be prior to the second time period. In some embodiments, computing device 102 may receive the first information and the second information from a first source (e.g., a device associated with a clinic, research organization, medical organization, etc.), and may also receive third information from a second source. For example, computing device 102 may receive the first information and the second information from a common entity (e.g., a same clinic, devices associated with a same medical organization, etc.). Alternatively, computing device 102 may receive the first information and the second information from different entities.

Computing device 102 may determine the second value using methods similar to the first value. For example, the second value may be a value of a patient parameter associated with the second information. In some embodiments, the second value may be a mean or median, a difference between a patient parameter value and historical data, or various other values that may be derived from the second information. It should be noted that patients represented in the data sets (e.g., represented in the first and second information) may not be identical. For example, the patients included in the first and second information may overlap completely, partially, or not at all. For example, in some embodiments, the at least one patient associated with the first value may be included in the plurality of patients (e.g., of the first information). In some embodiments, the at least one patient may be included in an additional plurality of patients (e.g., of the second information) and the at least one patient may not have been included in the plurality of patients (e.g., of the first information). In some embodiments, computing device 102 may output an amount of change between the first value and the second value (e.g., a standard deviation increasing by 0.2 with respect to a previous standard deviation).

At step 708, computing device 102 may detect, based on analysis of at least the first value and the second value, a potential anomaly in the second value. The analysis may take several forms. For example, computing device 102 may determine that the second value exceeds a threshold and may, based on the determination that the second value exceeds the threshold and/or a user input, classify the second value as a potential anomaly. In some embodiments, detecting the potential anomaly may be based on a comparison of a difference between the second value and the first value to a threshold. For example, if the second value exceeds the first value by more than a threshold amount, this may indicate the second value is anomalous.

In some embodiments, step 708 may further include determining a threshold. A threshold may be a value, expression, function, distribution, sequence, acceptable window of values, or other representation for setting a point at which information is classified with a particular classification (e.g., anomalous). For example, computing device 102 may determine, based on at least the first value of the patient parameter, a threshold for a patient parameter. By way of further example, the threshold may be based on a number (including a non-whole number, for example) of standard deviations from a mean or median of a plurality of values (e.g., historical values). In some embodiments, the threshold may be based on a number of standard deviations of a mean or median of the first difference and at least a second difference between derived values generated from the plurality of historical values. For example, the threshold may be based on a number of standard deviations from a mean or median of a first difference (e.g., between historical values) and at least a second difference (e.g., between historical values). In some embodiments, computing device 102 may determine the threshold based on a predetermined number of the plurality of patient datasets. For example, computing device 102 may be configured to determine the threshold after having received a predetermined quantity of patient information (e.g., data for a threshold number of patients). In some embodiments, computing device 102 may generate a graphical depiction of data points based on the first information (e.g., which may be used for display at step 710). In some embodiments, computing device 102 may also compute a line of best fit for the data points and may determine a threshold that is a predetermined tolerance distance from the line of best fit. Alternatively, computing device 102 may compute a function of best fit and may determine a threshold that is a predetermined tolerance distance from the function of best fit. In some embodiments, the threshold may set an amount of acceptable deviation for a percentile (e.g., determined at step 704).

In some embodiments, the threshold may be nuanced based on various pieces of information. For example, in some embodiments, the threshold may be based on a bias factor associated with a time of year. Such a bias factor may be determined based on historical values, and may be configured to compensate for periodic fluctuations in patient data (e.g., due to scheduled updates of patient information, such as to place patients within age groups), which may reduce a number of false positives of predicted anomalies. In some embodiments, determining the threshold for the patient parameter may include determining that the at least one patient is not included in the plurality of patients. For example, computing device 102 may determine that a patient is included in the second information who was not included in the first information (e.g., a new patient). Computing device 102 may use this determination to determine an appropriate threshold. For example, computing device 102 may operate a model that includes a parameter for new patients, which may automatically adjust the threshold implemented by the model, to reduce the number of false positive anomaly detections. In some embodiments, computing device 102 may determine that information for at least one patient is not included in the second information, and may modify the threshold based on the determination of that information for the at least one patient is not included in the second information. In this manner, the threshold may be adjusted to account for the removal of patient information, which may skew a value (e.g., a median of a dataset) toward a threshold, even though the patient information may not actually be anomalous following the removal of at least one patient (as patients may leave a trial or test, die, etc.).

In some embodiments, computing device 102 may update the threshold. For example, computing device 102 may update the threshold based on the second information. In some embodiments, computing device 102 may thus determine a threshold based on only the first information (e.g., a mean of the first information), only the second information (e.g., a median of the second information), a combination of both (e.g., a median of the first and second information together, possibly with the first and second information weighted differently), and/or a different combination of information. In some embodiments, multiple thresholds may be determined, and information may be compared to the multiple thresholds, to perform a multi-faceted approach for determining anomalies.

In some embodiments, the threshold may be determined based on at least one output from a machine learning model. For example, the machine learning model may be configured to predict the threshold using a function having a weight, vector, or coefficient based on at least one of: the first information, the second information, or a previous threshold associated with a previous patient parameter. By way of further example, a machine learning model may receive input data comprising synthetic data (e.g., training data) or actual data describing a number of parameters, such as patient data, threshold values, and classifications, and may determine an output (e.g., threshold, linear layer vector for generating a threshold, etc.) based on the input data. Additional details regarding the implementation of the trained machine learning model are provided above with respect to FIG. 3.

As described above, computing device 102 may receive a plurality of historical values associated with the patient parameter and the first value may be a mean or median of the plurality of historical values. Accordingly, the threshold may be based on a number of standard deviations from the mean or median of the plurality of historical values. As another example, the first value may be a first difference between derived values generated from the plurality of historical values associated with the patient parameter. In such embodiments, the threshold may be based on a number of standard deviations of a mean or median of the first difference and at least a second difference between derived values generated from the plurality of historical values.

In some embodiments, computing device 102 may determine that patient information (e.g., the second information) is anomalous based on determining that the second value is anomalous. In some embodiments, computing device 102 may determine that patient information (e.g., the second information) is anomalous based on analyzing multiple values. For example, computing device 102 may determine that a second value for patient information does not exceed a first threshold and that a third value for patient information does not exceed a second threshold, but may determine that multiple values, examined collectively, exceed a third threshold (e.g., an acceptable envelope described by an expression).

Computing device 102 may also determine that a third value for an additional patient parameter exceeds an additional threshold and may identify (e.g., predict) the third value exceeding the additional threshold as a second anomaly (e.g., a predicted second anomaly). In some embodiments, computing device 102 may determine additional information associated with anomalies. For example, computing device 102 may determine a first degree of severity of the first anomaly and/or may determine a second degree of severity of the second anomaly. A degree of severity may be based on a deviation of anomalous data from a threshold (e.g., a number of standard deviations away from a threshold). Computing device 102 may also rank the first and second anomalies based on the first and second degrees of severity. In some embodiments, computing device 102 may display the ranked first and second anomalies within the graphical user interface or an additional graphical user interface. In some embodiments, the first and second degrees of severity may be based on at least one of: a number of patients associated with the first and second anomalies, a type of patient associated with the first and second anomalies, or a first degree of deviation of the second value from the threshold and a second degree of deviation of the third value from the additional threshold.

In some embodiments, computing device 102 may determine an additional anomaly based on third information. For example, computing device 102 may use a first threshold to determine an anomaly based on first and second information from a first source (e.g., two patient datasets), and may use a second threshold, which may be based on the first threshold, to determine a second anomaly based on third information from a second source (e.g., another patient dataset related to a patient parameter of patient datasets from the first source).

In some embodiments, computing device 102 may determine a third value for an additional patient parameter (e.g., a patient parameter different from the patient parameter of the first value), which may be based on the first information. Computing device 102 may also determine, based on the first information, an additional threshold for the third value of the additional patient parameter. For example, the additional threshold may be used by computing device 102 to predict whether the third value is anomalous. In some embodiments, computing device 102 may predict, using a machine learning model, whether a third value is anomalous.

At step 710, computing device 102 may cause a graphical user interface to display at least one graphical element indicating the potential anomaly. For example, computing device 102 may, based on a comparison of the second value to the threshold, cause a graphical user interface to display at least one graphical element. To further this example, computing device 102 may determine that the second value exceeds the threshold, and may, based on the determination that the second value exceeds the threshold, cause the graphical user interface to display the at least one graphical element. In some embodiments, the graphical user element may comprise a comparison of the second value to the threshold. By way of example, the at least one graphical element may depict the comparison of the second value to the threshold (or a difference between the first and second value to a threshold) and may comprise at least one of: a color, a number, a table element, or an icon. As yet another example, in addition to or instead of the graphical user elements mentioned above (including with respect to FIGS. 4A-6B), computing device 102 may display any combination of a button, a color, a graph, a table, a list, an animation, a pop-up window, a point, a line, and/or any other graphical element to display patient or anomaly information. For example, the at least one graphical element (e.g., point, line, text, etc.) may be part of a graph that depicts patient values over time (e.g., patient values associated with at least one of the first or second information). For example, a graphical user interface may display a graph showing a change from a first value to a second value, with a threshold represented as a horizontal line.

In some embodiments, computing device 102 may display at least one additional graphical user element within the graphical user interface. For example, computing device 102 may cause the graphical user interface to display an additional graphical user element that is associated with a prediction of a third value as anomalous. In some embodiments, the third value may be associated with third information. In some embodiments, the additional graphical user element may comprise a comparison of the third value to the additional threshold (discussed above). Additionally or alternatively, the additional graphical element may depict the anomaly or the additional anomaly. In some embodiments, computing device 102 may cause a display of a visual indication of the prediction of the third value as anomalous (e.g., coloring or shading a cell in a table to indicate the prediction of the third value as anomalous). As another example, computing device 102 may cause display of a graph having multiple lines associated with different patient groups and/or patient parameters. On at least one of the lines, computing device 102 may cause the display of an alert, a color, a shading, a bolding, and/or other emphasizing feature to show an anomaly (e.g., predicted anomaly) associated with a patient group and/or patient parameter corresponding to the line. Thus, computing device 102 may display an additional graphical element depicts the anomaly (e.g., a potential anomaly detected at step 708 for a first patient parameter) and/or the additional anomaly (e.g., second potential anomaly detected for a second patient parameter).

In some embodiments, process 700 may further include steps for validating the potential anomaly detected in step 708. It is to be understood that these steps are optional and may be omitted in some implementations. At step 712, computing device 102 may receive a user input. For example, computing device 102 may receive a user input via a graphical user interface (e.g., the graphical user interface displaying the graphical element of step 710). For example, the user input may comprise an indication that a prediction (e.g., predicted anomaly) is confirmed or rejected. Additionally or alternatively, a user input may direct computing device 102 to use or to not use particular information (e.g., a second patient dataset) to update a model.

At step 714, computing device 102 may determine a classification, which may be a classification of patient information, a comparison, or other characterization of the first and/or second information. In some embodiments, the classification may be based on user input received at step 712. In some embodiments, the classification may identify the second information as acceptable or not acceptable. Additionally or alternatively, computing device 102 may determine a classification of anomalous, non-anomalous, verified (e.g., for a verified anomaly), unverified, approved, unapproved, rejected (e.g., rejecting a predicted anomaly), legitimized, unconfirmable, etc.

In some embodiments, computing device 102 may determine a classification of the second value (e.g., determined at step 706), which may be based on the received user input (e.g., at step 712). For example, in some embodiments, computing device 102 may classify the second value as anomalous (e.g., verified anomalous). To further this example, computing device 102 may receive a user input in response to displaying a prediction of value and/or patient information as anomalous. As yet another example, a user may provide verification (e.g., at a touchscreen) of whether a prediction (e.g., a prediction by a model that a value is or is not anomalous) was correct. In some embodiments, a classification may be based on a model prediction without user input. In some embodiments, a first classification may be determined (e.g., predicted) by a model, and a user may verify or reject the first classification to determine a second classification. In this manner, a user device (e.g., computing device 101) may verify at least one predicted anomaly.

In some embodiments, computing device 102 may perform additional steps based on the determined classification. For example, if computing device 102 determines a classification of acceptable (or non-anomalous, verified, approved, legitimized, etc.), computing device 102 may perform an action, which may be based on the determination that the classification is acceptable. In some embodiments, the action may be an action to promote or further use of the second information in some way. For example, computing device 102 may transmit the second information to a client device 101, etc. In other words, computing device 102 may determine whether to transmit the second information (e.g., to a research entity) based on the classification of the second value (e.g., whether the second value is acceptable or not). As another example, computing device 102 may add at least a portion of the second information to the first information (e.g., aggregate patient data). In other words, computing device 102 may determine whether to add at least a portion of the second information to the first information based on the classification of the second value (e.g., aggregate a first and second patient dataset). In some embodiments, the action may include modifying the second information based on the user input confirming the second value represents an anomaly. For example, this may include removing the second value, flagging the second value in the second information, or any other modifications that may be performed based on the second information including an anomaly.

If computing device 102 determines a classification of unacceptable (or anomalous, unverified, unapproved, unconfirmable, etc.), computing device 102 may limit the second information. For example, computing device 102 may, based on the classification of the second value as anomalous, cause at least one graphical element to include an indication of the second value as anomalous. Such an indication may help ensure that a user and/or machine does not take a particular action (e.g., transmit data associated with anomaly). As another example, computing device 102 may tag data associated with the second value, to prevent the data from being aggregated with other patient data and/or prevent the data from being transmitted (e.g., to a research entity). Computing device 102 may determine whether to add at least a portion of the second information to the first information based on the classification of the second value.

In some embodiments, computing device 102 may determine whether to transmit the second information to a client device based on the classification of the second value. For example, if computing device 102 determines the second information includes anomalous data, it may not transmit the data to client device 101. In some embodiments, computing device 102 may generate an alert based on the classification of the second value (either as acceptable or not acceptable). For example, the alert may be transmitted to a user, administrator, third party affiliate, or other entity. In some embodiments, the determined classification may be presented to the user. For example, computing device 102 may classify the second value as anomalous; and, based on the classification of the second value as anomalous, cause the at least one graphical element to include an indication of the second value as anomalous. In some embodiments, alerts may be generated automatically as part of process 700. For example, an alert may be generated based on a classification of the second value as anomalous (or upon a confirmation of the second value being classified as anomalous). In some embodiments, alerts may be generated periodically (e.g., each minute, on an hourly basis, on a daily basis, on a weekly basis, or according to any other suitable time period). Accordingly, an alert may include multiple detected anomalies during the time period, or since a previous alert was generated. Alerts may be generated in various formats, such as through a notification displayed on a device (e.g., a push notification, etc.), via an electronic message format (e.g., email, SMS, a proprietary message or communication service such as Slack®, etc.), via an alert log (e.g., by storing alerts in a data structure), or in various other formats. In some embodiments, a report may be generated each time process 700 is performed and the report may indicate whether or not any anomalies were detected.

In some embodiments, process 700 may further include updating a model. For example, computing device 102 may update a model, which may be a model configured to predict whether patient information is anomalous (exemplary aspects of which are described above). In some embodiments, the model may be updated based on a determined classification. For example, computing device 102 may, based on the classification of the second value, update at least one parameter of machine learning model configured to predict whether patient information is anomalous. By way of further example, computing device 102 may designate patient data classified as verified anomalous or verified non-anomalous as training data, which may be used as an input to train a model. Such updates may cause a machine learning model to more accurately predict anomalies. The updated model may then be used to predict later anomalies. For example, computing device 102 may predict, using the machine learning model, that a third value is anomalous and cause a display of a visual indication of the prediction of the third value as anomalous.

The foregoing description has been presented for purposes of illustration. It is not exhaustive and is not limited to the precise forms or embodiments disclosed. Modifications and adaptations will be apparent to those skilled in the art from consideration of the specification and practice of the disclosed embodiments. Additionally, although aspects of the disclosed embodiments are described as being stored in memory, one skilled in the art will appreciate that these aspects can also be stored on other types of computer readable media, such as secondary storage devices, for example, hard disks or CD ROM, or other forms of RAM or ROM, USB media, DVD, Blu-ray, 4K Ultra HD Blu-ray, or other optical drive media.

Computer programs based on the written description and disclosed methods are within the skill of an experienced developer. The various programs or program modules can be created using any of the techniques known to one skilled in the art or can be designed in connection with existing software. For example, program sections or program modules can be designed in or by means of .Net Framework, .Net Compact Framework (and related languages, such as Visual Basic, C, etc.), Java, Python, R, C++, Objective-C, HTML, HTML/AJAX combinations, XML, or HTML with included Java applets.

Moreover, while illustrative embodiments have been described herein, the scope of any and all embodiments having equivalent elements, modifications, omissions, combinations (e.g., of aspects across various embodiments), adaptations and/or alterations as would be appreciated by those skilled in the art based on the present disclosure. The limitations in the claims are to be interpreted broadly based on the language employed in the claims and not limited to examples described in the present specification or during the prosecution of the application. The examples are to be construed as non-exclusive. Furthermore, the steps of the disclosed methods may be modified in any manner, including by reordering, repeating, inserting, and/or deleting steps (including between steps of different processes). It is intended, therefore, that the specification and examples be considered as illustrative only, with a true scope and spirit being indicated by the following claims and their full scope of equivalents.

What is claimed is:

1. A system for classifying patient parameter values, the system comprising: at least one processor programmed to: access first information associated with a plurality of patients, the first information including a plurality of patient parameters associated with the plurality of patients, the first information being accessed electronically via a database; determine a first value associated with a patient parameter of at least one of the plurality of patients, the first value including a first statistical value determined based on the first information; analyze second information associated with the at least one patient to determine a second value of the patient parameter, the second value including a second statistical value determined based on the second information; train a machine learning model using a training data set, wherein the training data set comprises the first value and the second value, and wherein the machine learning model is configured to predict threshold values based on the first information and the second information; determine a threshold based on application of the machine learning model; detect, based at least on a comparison of a difference between at least the first value and the second value to the threshold, a potential anomaly in the second value, the potential anomaly indicating the second value is not attributed to a condition of the patient and represents a potential error in a dataset including the second value; cause a graphical user interface of a computing device to display at least one graphical element indicating the potential anomaly, the at least one graphical element including a color indicating a likelihood of the potential anomaly and an indicator displayed in association with data of an entity to indicate the data is potentially anomalous, the entity being a source of the dataset including the second value; receive, via the graphical user interface, a user input confirming whether the second value represents an anomaly; and determine a classification of the second value based on the received user input.

2. The system of claim 1, wherein the at least one processor is further programmed to modify the second information based on the user input confirming the second value represents an anomaly.

3. The system of claim 1, wherein the at least one processor is further programmed to update, based on the classification of the second value, at least one parameter of the machine learning model.

4. The system of claim 1, wherein the at least one processor is further programmed to:
classify the second value as anomalous; and
based on the classification of the second value as anomalous, cause the at least one graphical element to include an indication of the second value as anomalous.

5. The system of claim 1, wherein the at least one processor is further programmed to:
receive the first information during a first time period; and
receive the second information during a second time period, wherein the first time period is prior to the second time period.

6. The system of claim 1, wherein:
the at least one processor is further programmed to receive a plurality of historical values associated with the patient parameter; and
the first value is a mean or median of the plurality of historical values.

7. The system of claim 1, wherein:
the first information includes a plurality of patient datasets; and
the at least one processor is further programmed to determine the threshold based on a predetermined number of the plurality of patient datasets.

8. The system of claim 1, wherein the machine learning model is configured to predict the threshold using a function having a weight, vector, or coefficient based on at least one of: the first information, the second information, or a previous threshold associated with a previous patient parameter.

9. The system of claim 1, wherein the at least one processor is further programmed to:
determine that information for the at least one patient is missing from the second information; and
modify the threshold based on the determination of that information for the at least one patient is missing from the second information.

10. The system of claim 1, wherein the at least one processor is further programmed to:
determine that the second value exceeds the threshold;
based on the determination that the second value exceeds the threshold, classify the second value as a first anomaly;
determine that a third value for an additional patient parameter exceeds an additional threshold;
identify the third value exceeding the additional threshold as a second anomaly;
determine a first degree of severity of the first anomaly;
determine a second degree of severity of the second anomaly;
rank the first and second anomalies based on the first and second degrees of severity; and
display the ranked first and second anomalies within the graphical user interface or an additional graphical user interface.

11. The system of claim 10, wherein the first and second degrees of severity are based on at least one of: a number of patients associated with the first and second anomalies, a type of patient associated with the first and second anomalies, or a first degree of deviation of the second value from the threshold and a second degree of deviation of the third value from the additional threshold.

12. The system of claim 1, wherein the at least one processor is further programmed to:
determine that the second value exceeds the threshold; and
identify the second value exceeding the threshold as an anomaly.

13. The system of claim 12, wherein
the at least one processor is further programmed to:
receive the first information and the second information from a first source;
receive third information from a second source;

determine an additional anomaly based on the third information; and display within the graphical user interface at least one additional graphical element.

14. A method for classifying patient parameter values, comprising: accessing first information associated with a plurality of patients, the first information including a plurality of patient parameters associated with the plurality of patients, the first information being accessed electronically via a database; determining a first value associated with a patient parameter of at least one of the plurality of patients, the first value including a first statistical value determined based on the first information; analyzing second information associated with the at least one patient to determine a second value of the patient parameter, the second value including a second statistical value determined based on the second information; training a machine learning model using a training data set, wherein the training data set comprises the first value and the second value, and wherein the machine learning model is configured to predict threshold values based on the first information and the second information; determining, a threshold based on application of the machine learning model; detecting, based at least on a comparison of a difference between at least the first value and the second value to the threshold, a potential anomaly in the second value, the potential anomaly indicating the second value is not attributed to a condition of the patient and represents a potential error in a dataset including the second value; causing a graphical user interface of a computing device to display at least one graphical element indicating the potential anomaly, the at least one graphical element including a color indicating a likelihood of the potential anomaly and an indicator displayed in association with data of an entity to indicate the data is potentially anomalous, the entity being a source of the dataset including the second value; receiving, via the graphical user interface, a user input confirming whether the second value represents an anomaly; and receiving, via the graphical user interface, a user input confirming whether the second value represents an anomaly; and determining a classification of the second value based on the received user input.

15. A non-transitory computer-readable medium comprising instructions that when executed by one or more processors, cause the one or more processors to: access first information associated with a plurality of patients, the first information including a plurality of patient parameters associated with the plurality of patients, the first information being accessed electronically via a database; determine a first value associated with a patient parameter of at least one of the plurality of patients, the first value including a first statistical value determined based on the first information; analyze second information associated with the at least one patient to determine a second value of the patient parameter, the second value including a second statistical value determined based on the second information; train a machine learning model using a training data set, wherein the training data set comprises the first value and the second value, and wherein the machine learning model is configured to predict threshold values based on the first information and the second information; determine a threshold based on application of the machine learning model; detect, based at least on a comparison of a difference between at least the first value and the second value to the threshold, a potential anomaly in the second value, the potential anomaly indicating the second value is not attributed to a condition of the patient and represents a potential error in a dataset including the second value; cause a graphical user interface of a computing device to display at least one graphical element indicating the potential anomaly, the at least one graphical element including a color indicating a likelihood of the potential anomaly and an indicator displayed in association with data of an entity to indicate the data is potentially anomalous, the entity being a source of the dataset including the second value; receiving, via the graphical user interface, a user input confirming whether the second value represents an anomaly; and receiving, via the graphical user interface, a user input confirming whether the second value represents an anomaly; and determining a classification of the second value based on the received user input.

* * * * *